US011426428B2

(12) United States Patent
Lee

(10) Patent No.: US 11,426,428 B2
(45) Date of Patent: Aug. 30, 2022

(54) METHODS FOR IMPROVING RESPIRATORY SYSTEM HEALTH AND INCREASING THE CONCENTRATION OF HYPOTHIOCYANATE ION IN VERTEBRATE LUNGS

(71) Applicant: James D. Lee, Kansas City, KS (US)

(72) Inventor: James D. Lee, Kansas City, KS (US)

(73) Assignee: SYNEXIS LLC, Lenexa, KS (US)

( * ) Notice: Subject to any disclaimer, the term of this patent is extended or adjusted under 35 U.S.C. 154(b) by 0 days.

(21) Appl. No.: 16/431,032

(22) Filed: Jun. 4, 2019

(65) Prior Publication Data
US 2019/0336526 A1  Nov. 7, 2019

Related U.S. Application Data

(63) Continuation of application No. 14/913,286, filed as application No. PCT/US2014/051914 on Aug. 20, 2014, now abandoned.
(Continued)

(51) Int. Cl.
*A61K 33/40* (2006.01)
*A61L 9/04* (2006.01)
*A61L 2/20* (2006.01)

(52) U.S. Cl.
CPC ............ *A61K 33/40* (2013.01); *A61L 2/208* (2013.01); *A61L 9/04* (2013.01); *A61L 2202/11* (2013.01); *A61L 2209/211* (2013.01)

(58) Field of Classification Search
CPC ........ A61L 2/208; A61L 9/04; A61L 2202/11; A61L 2209/211; A61P 11/00; A61P 37/08; A61P 31/00; A61K 33/40
See application file for complete search history.

(56) References Cited

U.S. PATENT DOCUMENTS 7,407,633 B2  8/2008  Potember et al.
7,988,923 B2  8/2011  Fink et al.
(Continued)

FOREIGN PATENT DOCUMENTS

CN  101854958 A  10/2010
CN  109589441 A1  4/2019
(Continued)

OTHER PUBLICATIONS

"Beat Sinus Infections Without Antibiotics," Healthy Doctors Teach You How to Be Healthy, available at healthydoctors.com/beat-sinus-infections-without-antibiotics/ obtained Oct. 2, 2018, in U.S. Appl. No. 14/913,286.
(Continued)

*Primary Examiner* — Jianfeng Song
(74) *Attorney, Agent, or Firm* — McBee Moore & Vanik IP, LLC; Susan McBee; Brett Stauffer

(57) ABSTRACT

The present disclosure relates to methods and devices to improve respiratory system health, increase resistance to infection, and increase the hypothiocyanate ion in mammalian lungs. The methods generally comprise: generating a Hydrogen Peroxide Gas that is non-hydrated and free of ozone, and directing the gas comprising primarily Hydrogen Peroxide Gas into an environment and exposing a subject to the environment such that the Hydrogen Peroxide Gas acts to the increase of the hypothiocyanate ion in mammalian lungs.

10 Claims, 9 Drawing Sheets

Related U.S. Application Data

(60) Provisional application No. 61/867,971, filed on Aug. 20, 2013.

(56) References Cited

U.S. PATENT DOCUMENTS

| | | | |
|---|---|---|---|
| 8,012,412 | B2 | 9/2011 | Normark et al. |
| 8,168,122 | B2* | 5/2012 | Lee .......................... B01J 7/02 422/120 |
| 8,658,101 | B1 | 2/2014 | Burnett |
| 8,658,329 | B2 | 2/2014 | Kim et al. |
| 8,877,046 | B2 | 11/2014 | Ellis |
| 9,034,255 | B2 | 5/2015 | Lee |
| 9,283,295 | B2 | 3/2016 | Fink et al. |
| 9,295,746 | B2 | 3/2016 | Ellis |
| 9,364,571 | B2 | 6/2016 | Ahiska |
| 9,433,691 | B2 | 9/2016 | Eide et al. |
| 9,839,901 | B2 | 12/2017 | Ellis et al. |
| 2005/0191205 | A1 | 9/2005 | Uslenghi et al. |
| 2006/0008379 | A1 | 1/2006 | Mielnik et al. |
| 2006/0269438 | A1 | 11/2006 | Lagunas-Solar et al. |
| 2009/0041617 | A1 | 2/2009 | Lee |
| 2011/0182772 | A1 | 7/2011 | Holt |
| 2011/0182773 | A1 | 7/2011 | Holt |
| 2011/0183598 | A1 | 7/2011 | Holt |
| 2012/0020832 | A1 | 1/2012 | St. Onge et al. |
| 2020/0368713 | A1 | 11/2020 | Holt |
| 2021/0038755 | A1 | 2/2021 | Eide |
| 2021/0228762 | A1 | 7/2021 | Eide et al. |
| 2021/0346565 | A1 | 11/2021 | Woodbridge |

FOREIGN PATENT DOCUMENTS

| | | |
|---|---|---|
| EP | 0 826 531 A2 | 3/1998 |
| JP | 2008-183182 | 8/2008 |
| JP | WO 2008-183182 | 8/2008 |
| JP | 2010-535807 A | 11/2010 |
| JP | 2016-537144 | 12/2016 |
| MX | 291245 | 8/2011 |
| RU | 2035919 C1 | 5/1995 |
| WO | WO 2002/016010 A1 | 2/2002 |
| WO | WO 2007/008205 A1 | 1/2007 |
| WO | WO 2008/063252 A2 | 5/2008 |
| WO | WO 2009/021108 A1 | 2/2009 |
| WO | WO 2010/093796 A1 | 8/2010 |
| WO | WO 2011/017030 A2 | 2/2011 |
| WO | WO 2014/186805 A1 | 11/2014 |
| WO | WO 2015/026958 | 2/2015 |
| WO | WO 2015/171633 | 11/2015 |
| WO | WO 2016/172223 | 10/2016 |
| WO | WO 2016/176486 | 11/2016 |
| WO | WO 2018/129537 | 7/2018 |

OTHER PUBLICATIONS

Block, "Disinfection, sterilization, and preservation," Disinfection, Sterilization and Preservation, pp. 187-191 and 344 (2001), in U.S. Appl. No. 14/913,286.

Crawford, "A review of the animal welfare enforcement report data, 1973-1995," A WIC Newsletter, 7(2) Summer 1996, in U.S. Appl. No. 14/913,286.

"Do-It-Yourself Oxidation Therapy to Fight the Flu," Healthy Doctors Teach You How To Be Healthy, available at healthydoctors.com/do-it-yourself-oxidation-therapy-to-fight-the-flu/ obtained Oct. 2, 2018, in U.S. Appl. No. 14/913,286.

El-Chemaly et al., "Hydrogen Peroxide-Scavenging Properties of Normal Human Airway Secretions," *American Journal of Respiratory and Critical Care Medicine*, 167:425-430 (2003), in U.S. Appl. No. 14/913,286.

Ernstgard et al., "Acute effects of exposure to vapors of hydrogen peroxide in humans," *Toxicology Letters* 4.212:222-227 (2012), in U.S. Appl. No. 14/913,286.

Healthydoctors ("Do-It Yourself Oxidation Therapy to Flight the Flu," Feb. 3, 2010, retrieved from https://healthydoctors.com/do-it-yourself-oxidation-therapy-to-fight-the-flu, in U.S. Appl. No. 14/913,286.

Herman et al., APIC Poster, Pocono Medical Center and Pocono Health System and The Commonwealth Medical College (2015), in U.S. Appl. No. 14/913,286.

"High-Strength Hydrogen Peroxide Specifications," State Standard of the Russian Federation, GOSTTANDART of Russia Moscow, p. 50632-93, dated Jan. 1, 1995, in U.S. Appl. No. 14/913,286.

International Search Report and Written Opinion issued in International Application No. PCT/US2014/051914 dated Nov. 17, 2014, in U.S. Appl. No. 14/913,286.

Kubasov et al., "Electrochemical Technology of Inorganic Substances," Moscow Chemistry, p. 179 (1989), in U.S. Appl. No. 14/913,286.

"Medical Disclaimer," Healthy Doctors Teach You How to Be Healthy available at healthydoctors.com/medical-disclaimer/ obtained Oct. 2, 2018, in U.S. Appl. No. 14/913,286.

Morio et al., "Tissue Injury Following Inhalation of Fine Particulate Matter and Hydrogen Peroxide Is Associated with Altered Production of Inflammatory mediators and Antioxidants by Alveolar Macrophages," *Toxicology and Applied Pharmacology* V. 177:188-199 (2001), in U.S. Appl. No. 14/913,286.

"One of the Worst Side Effects of Alternative Therapies—and How to Protect Yourself," Healthy Doctors Teach You How to Be Healthy, available at healthydoctors.com/one-of-the-worst-side-effects-of-alternative-therapeis-and-how-to-protect-yourself/ obtained Oct. 2, 2018, in U.S. Appl. No. 14/913,286.

Pruitt et al., "Lactoperoxidase-catalyzed oxidation of thiocyanate: polarographic study of the oxidation products," *Biochemistry*,21(3):562-561 (1982), in U.S. Appl. No. 14/913,286.

"Robert Rowen MD Influenza and You Update Jan. 13, 2015," Healthy Doctors Teach You How to Be Healthy, available at healthydoctors.com/robert-rowen-md-influenza-and-you-update-1-13-15/ obtained Oct. 2, 2018, in U.S. Appl. No. 14/913,286.

Search Report and Written Opinion dated Feb. 28, 2017 in Singapore Appln. 11201601053W, in U.S. Appl. No. 14/913,286.

Search Report dated Jul. 3, 2018, in Russian Patent Application No. 2016109797 (with English translation), in U.S. Appl. No. 14/913,286.

Search Report dated Aug. 3, 2017, in Chinese Patent Application No. 201480057650.8 (with English translation), in U.S. Appl. No. 14/913,286.

Siddons, "Hydrogen Peroxide Therapy," How Hydrogen Peroxide Therapy Works/HowStuffWorks available at health.howstuffworkds.com/wellness/natural-medicine/alternative/hydrogen-peroxide-therapy.htm/printable obtained Oct. 2, 2018, in U.S. Appl. No. 14/913,286.

Spiegel, "Evidence-Based Medicine: Perspectives for Homotoxicology," pp. 40-43, 47-49 (2004), in U.S. Appl. No. 14/913,286.

Thomas et al., "Lactoperoxidase, peroxide, thiocyanate antimicrobial system: correlation of sulfhydryl oxidation with antimicrobial action," *Infec. Immun.*, 20(2):456-463 (1978), in U.S. Appl. No. 14/913,286.

Warning Letter, *Frad 35, Inc.* Department of Health and Human Services, Public Health Service, Food and Drug Administration (2006), in U.S. Appl. No. 14/913,286.

White et al., "Peroxidase-Thiocyanate-Peroxide Antibacterial System Does Not Damage DNA," *Antimicrob. Agents Chemother.*, 23(2):267-272 (1983), in U.S. Appl. No. 14/913,286.

Czepiel et al., "Clostridium difficile infection: review," *Eur J Clin Microbiol Infect Dis.* 38(7): 1211-1221 (2019).

Tacconelli, "Vancomycin-resistant enterococci (VRE): transmission and control," *International Journal of Antimicrobial Agents* 31(2):99-106 (2008).

"Types of chemical disinfects used in hospitals," downloaded from the internet at monib-health[dot]com/en/post/91-chemical-disinfectants-used-in-hospitals (2021).

Tacconelli, "Vancomycin-resistant enterococci (VRE): transmission and control," International Journal of Antimicrobial Agents 31(2):2008.

"Types of chemical disinfects used in hospitals," downloaded from https://monib-health[dot]com/en/post/91-chemical-disinfectants-used-in-hospitals (2021).

* cited by examiner

METHODS FOR IMPROVING RESPIRATORY SYSTEM HEALTH AND INCREASING THE CONCENTRATION OF HYPOTHIOCYANATE ION IN VERTEBRATE LUNGS

CROSS-REFERENCE TO RELATED APPLICATIONS

This application is a continuation of U.S. application Ser. No. 14/913,286, filed Feb. 19, 2016, which is a National Stage aapliction of International Application No. PCT/US2014/051914 filed Aug. 20, 2014, which claims priority from U.S. Provisional Patent Application No. 61/867,971, filed Aug. 20, 2013, and which are hereby incorporated by reference in their entirety.

FIELD OF THE INVENTION

This disclosure relates to methods for improving respiratory system health in subjects by providing habitable environments comprising purified hydrogen peroxide gas (PHPG) that is free of hydration and ozone. The disclosure also relates to enclosed spaces, dwellings and environments for treatment, mitigation, and prevention of respiratory conditions including infections and chronic conditions.

BACKGROUND

The quality of the air in inhabited enclosed spaces plays an important role in promoting human health and safety. Air quality, as generally understood by people refers to considerations of the composition of the air and the presence or absence of various pollutants, allergens, pathogens, and parasites. The air quality in enclosed spaces impact a wide range of human conditions including asthma, chronic obstructive pulmonary disease (COPD), cystic fibrosis, bronchitis, sinusitis, tuberculosis, pneumonia, and myriad other diseases and pathologies of the respiratory system. Many infectious agents may be air borne as are various allergens and non-infectious pathogens and substances that can trigger adverse events and respiratory distress. Improving the quality of the air in the indoor environment can avoid, mitigate, or decrease the cost of pathological conditions of the respiratory system.

Risks of allergens, pathogens and parasites are not limited to indoor enclosed spaces, but often can be transmitted and spread more readily indoors. People spend a large majority of their time indoors. In the U.S., people spend approximately 90 percent of their time indoors. Of this, 69 percent of their time was spent at home, and 18 percent was spent in some other type of indoor venue, such as at a place of work. (U.S. Environmental Protection Agency. 1989. Report to Congress on indoor air quality: Volume 2. EPA/400/1-89/001C. Washington, D.C.)

Approaches to improve air quality generally include efforts to filter pathogens and allergens and the development of air handling systems that provide for effective, nontoxic and noncorrosive pathogen elimination technologies. Heating, ventilation and air conditioning (HVAC) systems in the art provide for neutralizing airborne pathogens by passing the contaminated air through separate enclosed systems that employ UV light, ozone, and other activated oxygen species to kill, neutralize or destroy both living and non-living pathogens. Examples of such approaches may be found, for example, in International Patent Publication WO 2002016010 and U.S. Pat. No. 7,407,633. Such HVAC systems are limited by the requirement that the air pass through the system in order to be effective. Pathogens, allergens, and parasites too heavy to traverse current air handling systems are missed.

There is a particular need to remove airborne pathogens from air handling systems in health care facilities including permanent facilities such as hospitals, nursing homes, and hospices, as well as temporary facilities established during health care crises. Epidemiological data demonstrates that the dissemination of respiratory diseases inside buildings, and specifically by ventilation systems, is a significant problem not addressed by current technologies. In addition to health care facilities, in times of crisis, including for example epidemics, pandemics, chemical, and biological attacks, there is a need for methods that reduce the transmission of infectious pathogens. The transmission of respiratory infections in indoor environments represents a major public health concern and prior efforts are limited to the isolated treatment of circulating air rather than treating the air in the enclosed environment in situ.

U.S. Pat. No. 8,168,122, issued May 1, 2012, and U.S. Pat. No. 8,685,329, issued Apr. 1, 2014, provide devices and methods for the production of purified hydrogen peroxide gas (PHPG) and the use of PHPG for microbial control, disinfection, and remediation of an environment. The specification further provides methods for generating a purified hydrogen peroxide gas (PHPG) that is free of hydration, ozone, plasma species, and/or organic species. Providing PHPG to an environment provides microbial control, disinfection, remediation, or combinations thereof, in the environment, preferably both on surfaces and in the air. U.S. Pat. Nos. 8,168,122 and 8,685,329 are hereby incorporated by reference in their entireties.

International Patent Application No. PCT/US2014/038652, filed May 19, 2014 (the '652 application), claiming priority to U.S. application Ser. No. 61/824,689, filed May 17, 2013, provides methods for the control of arthropods, including insects and arachnids, using PHPG. International Patent Application No. PCT/US2014/038652 is hereby incorporated by reference in its entirety.

International Patent Application No. PCT/US2008/072454, filed Aug. 7, 2008 (the '454 application), claiming priority to U.S. application Ser. No. 60/954,5669, filed Aug. 7, 2007, and U.S. application Ser. No. 61/031,580, filed Feb. 28, 2008, provides methods and devices for providing microbial control and/or disinfection/remediation of an environment. International Patent Application No. PCT/US2008/072454 is hereby incorporated by reference in its entirety.

International Patent Application No. PCT/US2010/023903, filed Feb. 11, 2010 (the '903 application), claiming priority to U.S. application Ser. No. 61/152,581, filed Feb. 13, 2009, and U.S. application Ser. No. 61/258,005, filed Nov. 4, 2009, provides methods and devices for providing microbial control and/or disinfection/remediation of an environment. International Patent Application No. PCT/US2010/023903 is hereby incorporated by reference in its entirety.

The respiratory tracts of vertebrate species include innate defenses against microorganisms and pathogens. Secreted mucus and frequent branchpoints of the bronchopulmonary tree trap inhaled pathogens which are expelled by the mucociliary escalator and cough reflex. The respiratory system also includes cellular defense mechanisms including leukocytes, antibodies and other aspects of the immune system. Other aspects of the innate defenses of the respiratory system include non-cellular, passive mechanisms residing in the secretions of the respiratory tract.

The respiratory tract includes secretions having antimicrobial activity. Among the secretions are immunoglobulins, complement factors, enzymes, and various binding proteins. Studies have demonstrated that a major component of the innate defense system is lactoperoxidase (LPO). LPO is present in many secretions and is found at high levels in airway secretions. See, El-Chemaly, et al., "Hydrogen Peroxide—Scavenging Properties of Normal Human Airway Secretions," *American Journal of Respiratory and Critical Care Medicine*, 167:425-430 (2003). LPO utilizes hydrogen peroxide to oxidize thiocyanate to hypothiocyanate:

$$H_2O_2 + SCN^- \rightarrow OSCN^- + H_2O$$

(Thomas et al., "Lactoperoxidase, peroxide, thiocyanate antimicrobial system: correlation of sulfhydryl oxidation with antimicrobial action," *Infec. Immun.* 20(2):456-63 (1978). Lactoperoxidase-catalyzed reactions yield short lived intermediary oxidation products of SCN-, providing antibacterial activity. Pruitt et al., "Lactoperoxidase-catalyzed oxidation of thiocyanate: polarographic study of the oxidation products,". *Biochemistry* 21 (3): 562-7 (1982). Thiocyanate is present in significant amounts in airway secretions. Reiter et al., "Lactoperoxidase: biological functions," in *Peroxidases in Chemistry and Biology*, Vol. I., J. Everse, K. E. Everse, and M. B. Grisham, editors, CRC Press. Boca Raton, Fla. pp. 144-180 (1991).

Hypothiocyanate exists in equilibrium with hypothiocyanous acid:

$$H^+ + OSCN^- \rightarrow HOSCN$$

The uncharged HOSCN is considered to be the greater bactericidal of the two forms. See, Thomas et al.. Not to be limited by theory, it is thought that the action of (OSCN)— against bacteria, and presumably other pathogens, is reported to be caused by sulfhydryls (SH) oxidation. See id. Among the effects observed in bacteria by the oxidation of —SH groups in the bacterial cytoplasmic membrane is a loss of the ability to transport glucose and leakage of potassium ions, amino acids and peptides. OSCN⁻ is non-mutagenic and is considered safe. See White et al., "Peroxidase-Thiocyanate-Peroxide Antibacterial System Does Not Damage DNA,"*Antimicrob. Agents Chemother.,* 23 (2): 267-72 (1983).

In the course of testing systems that provide PHPG to an indoor environment, it was observed that PHPG containing environments reduce the incidence of respiratory infection and improved chronic respiratory conditions in people intermittently occupying the spaces. Not to be limited by theory, it is thought that the improved health of subjects exposed to PHPG results from the increased formation of the antimicrobial hypothiocyanate in the secretions of the respiratory system. Surprisingly, it is observed that constant exposure of a subject to PHPG is not necessary to achieve improved respiratory health.

Using morphology that permits immediate removal of hydrogen peroxide gas before it can be reduced, gas hydrogen peroxide may be generated in any suitable manner known in the art, including but not limited to, any suitable process known in the art that simultaneously oxidizes water (or another compound that can provide hydrogen ions separable by osmosis) in liquid or gas form, and reduces oxygen gas, including gas phase photo-catalysis, e.g., using a metal catalyst such as titanium dioxide, zirconium oxide, titanium dioxide doped with cocatalysts (such as copper, rhodium, silver, platinum, gold, etc.), or other suitable metal oxide photocatalysts. Purified gas hydrogen peroxide gas may also be produced by electrolytic processes using anodes and cathodes made from any suitable metal, or constructed from metal oxide ceramics using morphology that permits immediate removal of hydrogen peroxide gas before it can be reduced. Alternatively, hydrogen peroxide gas may be produced by high frequency excitation of gaseous water and oxygen molecules on a suitable supporting substrate using morphology that permits immediate removal of hydrogen peroxide gas before it can be reduced.

SUMMARY OF THE INVENTION

The present disclosure provides for, and includes, enclosed spaces for human or veterinary use comprising purified hydrogen peroxide gas (PHPG) at a concentration of at least 0.01 parts per million wherein said PHPG is non-hydrated and free of ozone.

In another aspect, the present disclosure provides for, and includes, dwellings having purified hydrogen peroxide gas (PHPG) at concentration of at least 0.01 parts per million wherein said PHPG is non-hydrated and free of ozone.

In a further aspect, the present disclosure provides for, and includes, a method for preparing a purified hydrogen peroxide gas (PHPG) containing environment comprising generating PHPG that is substantially free of hydration and ozone, and accumulating said PHPG until a final concentration of at least 0.01 parts per million (ppm) is achieved.

In an aspect, the present disclosure provides for, and includes, a method for preparing a purified hydrogen peroxide gas (PHPG) containing environment comprising generating PHPG that is substantially free of hydration and ozone, and accumulating said PHPG until a final concentration of at least 0.01 parts per million (ppm) is achieved.

In an aspect, the present disclosure provides for, and includes, a method for providing an enclosed space comprising a purified hydrogen peroxide gas (PHPG) comprising providing PHPG that is substantially free of hydration and ozone to said environment at a rate sufficient to maintain PHPG gas at a final concentration of at least 0.01 parts per million (ppm).

In an aspect, the present disclosure provides for, and includes, a method of treatment comprising providing a treatment environment comprising an enclosed space suitable for habitation wherein said treatment environment comprises a purified hydrogen peroxide gas (PHPG) concentration of at least 0.01 parts per million and the PHPG is non-hydrated and free of ozone and exposing a subject in need of treatment to the treatment environment for a treatment period.

In an aspect, the present disclosure provides for, and includes, a method for treating a respiratory illness in a subject comprising providing an environment comprising a purified hydrogen peroxide gas (PHPG) that is substantially free of hydration and ozone at a final concentration of at least 0.01 parts per million (ppm) and exposing the subject to the environment for at least one period of time, wherein the treating comprises reducing the severity of a respiratory infection, reducing the duration of a respiratory infection, reducing the severity of an allergy, preventing transmission of a respiratory infection, reducing transmission of a respiratory infection in a population, improving lung function, or any combination thereof.

In an aspect, the present disclosure provides for, and includes, a method for treating a respiratory condition in a subject in need thereof comprising providing the subject in need with an environment comprising a purified hydrogen peroxide gas (PHPG) that is substantially free of hydration and ozone at a final concentration of at least 0.01 parts per million (ppm).

In an aspect, the present disclosure provides for, and includes, a method for reducing the severity of a respiratory infection in a subject comprising providing a purified hydrogen peroxide gas (PHPG) containing environment comprising PHPG that is substantially free of hydration and ozone at a final concentration of at least 0.01 parts per million (ppm), and exposing the subject to the PHPG containing environment for a period of time, wherein the severity of the respiratory infection is reduced.

In an aspect, the present disclosure provides for, and includes, a generating a purified hydrogen peroxide gas (PHPG) that is substantially free of hydration and ozone to an environment, wherein the environment accumulates the PHPG at a final concentration of at least 0.01 parts per million, and exposing the subject to the PHPG containing environment for a period of time.

In an aspect, the present disclosure provides for, and includes, a method for preventing a respiratory infection comprising generating a hydrogen peroxide gas that is substantially free of hydration and ozone and providing the hydrogen peroxide gas to an environment wherein the environment accumulates the PHPG at a final concentration of at least 0.01 parts per million and chronically exposing an animal at risk for respiratory infection to the environment.

In an aspect, the present disclosure provides for, and includes, a method for reducing the transmission of a respiratory infection from a first subject having the respiratory infection to a second subject not having the respiratory infection comprising providing an environment comprising a purified hydrogen peroxide gas (PHPG) that is substantially free of hydration and ozone at a final concentration of at least 0.01 parts per million and exposing the first subject having the respiratory infection to the environment for one or more periods of time.

In an aspect, the present disclosure provides for, and includes, a method of supplementing endogenous H2O2 in the lung of a subject comprising exposing the subject to an environment comprising a purified hydrogen peroxide gas (PHPG) that is substantially free of hydration and ozone, wherein the environment accumulates the PHPG at a final concentration of at least 0.01 parts per million.

In an aspect, the present disclosure provides for, and includes, a method for enhancing host defenses to a respiratory infection of a subject comprising providing an environment comprising a purified hydrogen peroxide gas (PHPG) that is substantially free of hydration and ozone at a final concentration of at least 0.01 parts per million and exposing the subject to the environment for one or more periods of time, thereby increasing the level of hypothiocyanate ion in the lungs of the subject.

In an aspect, the present disclosure provides for, and includes, a method for stimulating the host defenses to a respiratory infection of a subject comprising providing an environment comprising a purified hydrogen peroxide gas (PHPG) that is substantially free of hydration and ozone at a final concentration of at least 0.01 parts per million and exposing the subject to the environment for one or more periods of time, thereby increasing the level of hypothiocyanate ion in the lungs of the subject.

In an aspect, the present disclosure provides for, and includes, a method of managing a condition affecting the lungs of a subject comprising generating a purified hydrogen peroxide gas (PHPG) that is substantially free of hydration and ozone to an environment wherein the environment accumulates the PHPG at a final concentration of at least 0.01 parts per million, and exposing the subject to the PHPG containing environment for a period of time.

In an aspect, the present disclosure provides for, and includes, a method of decreasing the severity of a respiratory infection in a subject comprising providing an environment comprising a purified hydrogen peroxide gas (PHPG) that is substantially free of hydration and ozone at a final concentration of at least 0.01 parts per million and exposing the subject to the environment for one or more periods of time, wherein the severity of the respiratory infection is decreased.

In an aspect, the present disclosure provides for, and includes, a method of increasing the rate of hypothiocyanate ion production catalyzed by lactoperoxidase (LPO) in the lungs of a subject comprising providing an environment comprising a purified hydrogen peroxide gas (PHPG) that is substantially free of hydration and ozone at a final concentration of at least 0.01 parts per million and exposing the subject to the environment for one or more periods of time.

In an aspect, the present disclosure provides for, and includes, a method of improving the lung function of a subject comprising providing an environment comprising a purified hydrogen peroxide gas (PHPG) that is substantially free of hydration and ozone at a final concentration of at least 0.01 parts per million and exposing the subject to the environment for one or more periods of time.

In an aspect, the present disclosure provides for, and includes, the use of a purified hydrogen peroxide gas (PHPG) for the preparation of an environment suitable for preventing, treating, or controlling a respiratory illness in a subject comprising generating a hydrogen peroxide gas that is substantially free of hydration and ozone and providing the hydrogen peroxide gas to an environment wherein the environment accumulates the PHPG at a final concentration of at least 0.01 parts per million.

In an aspect, the present disclosure provides for, and includes, a method for preparing an environment suitable for occupancy of a subject comprising providing a device for producing purified hydrogen peroxide gas (PHPG), wherein the PHPG is substantially free of hydration and ozone, and wherein the environment has a reduced level of infectious agents, allergens, or a combination thereof.

DETAILED DESCRIPTION

Figure 1A:
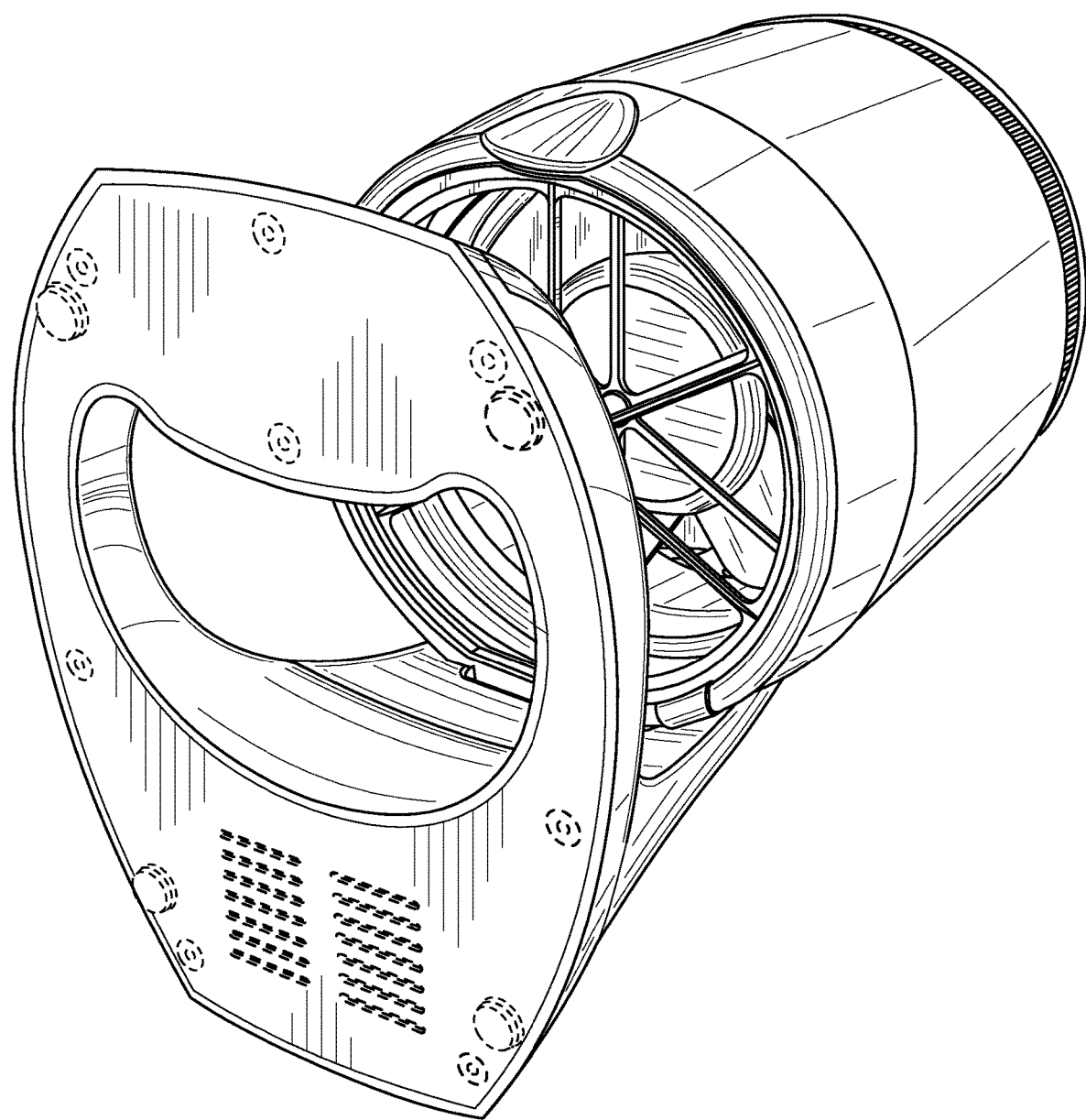
FIGS. 1A-D illustrate an exemplary standalone device for providing PHPG that is substantially free of hydration and ozone PHPG to an environment according to the present disclosure.
Figure 1B:
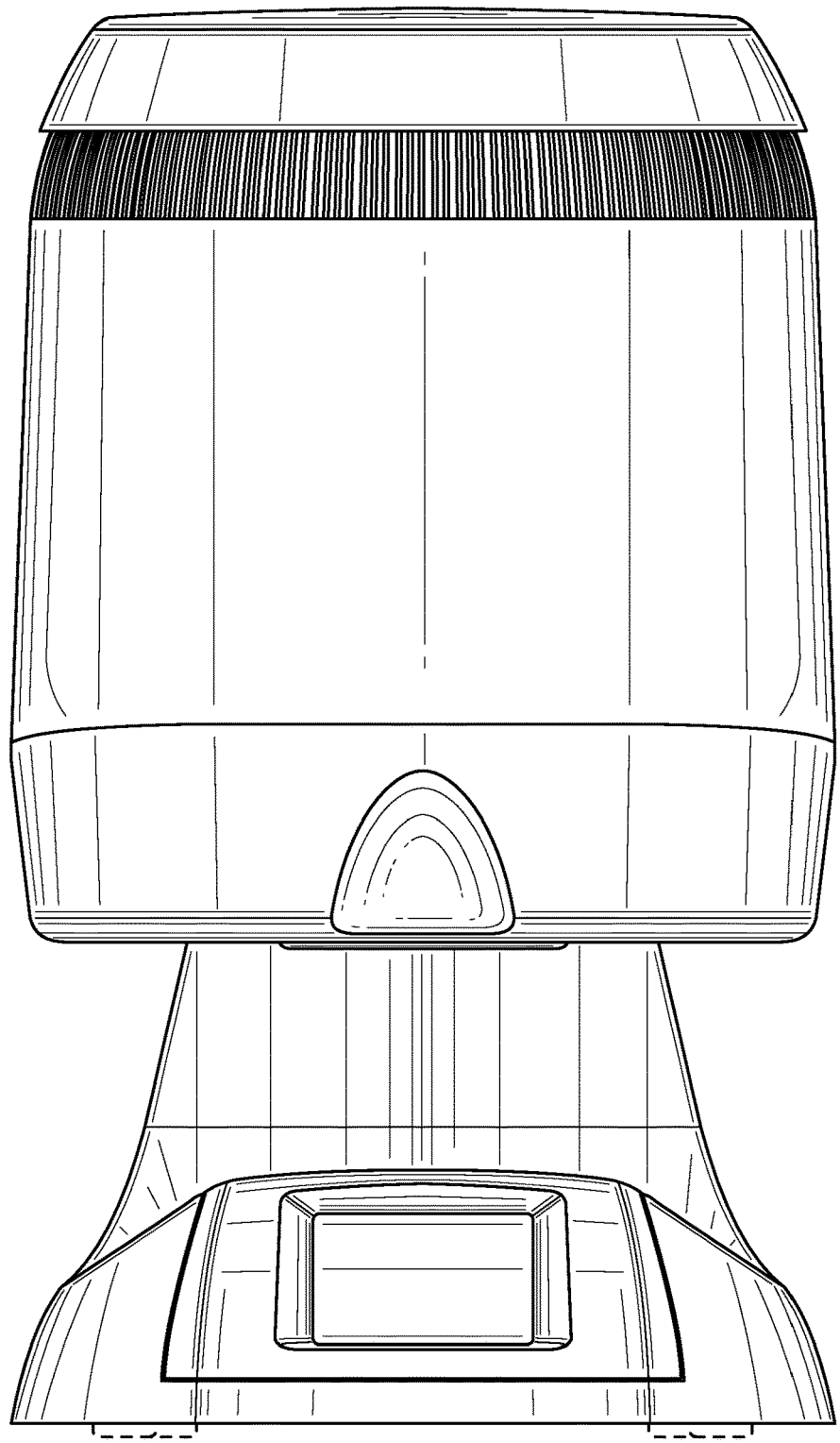
Figure 1C:
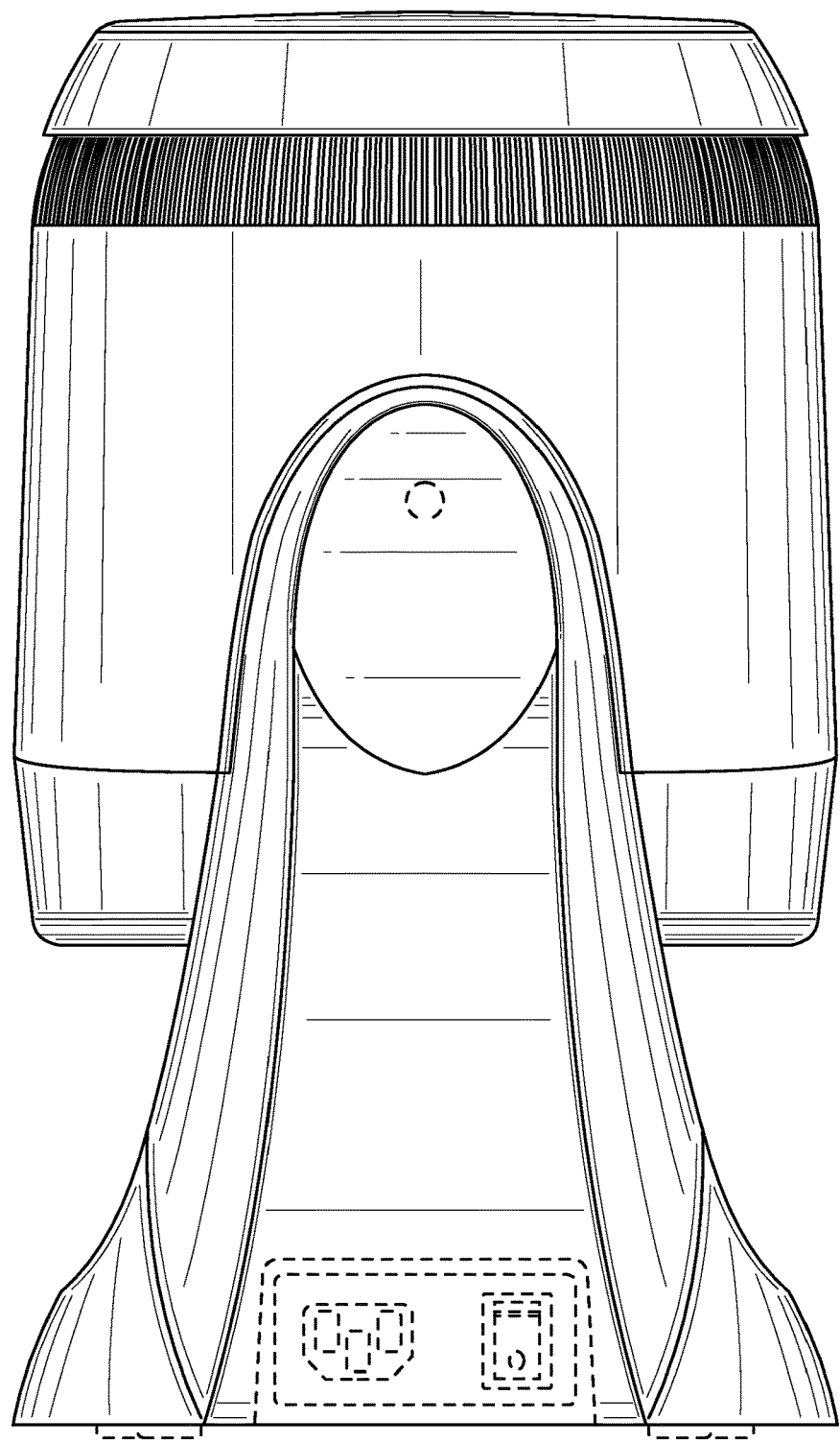
Figure 1D:
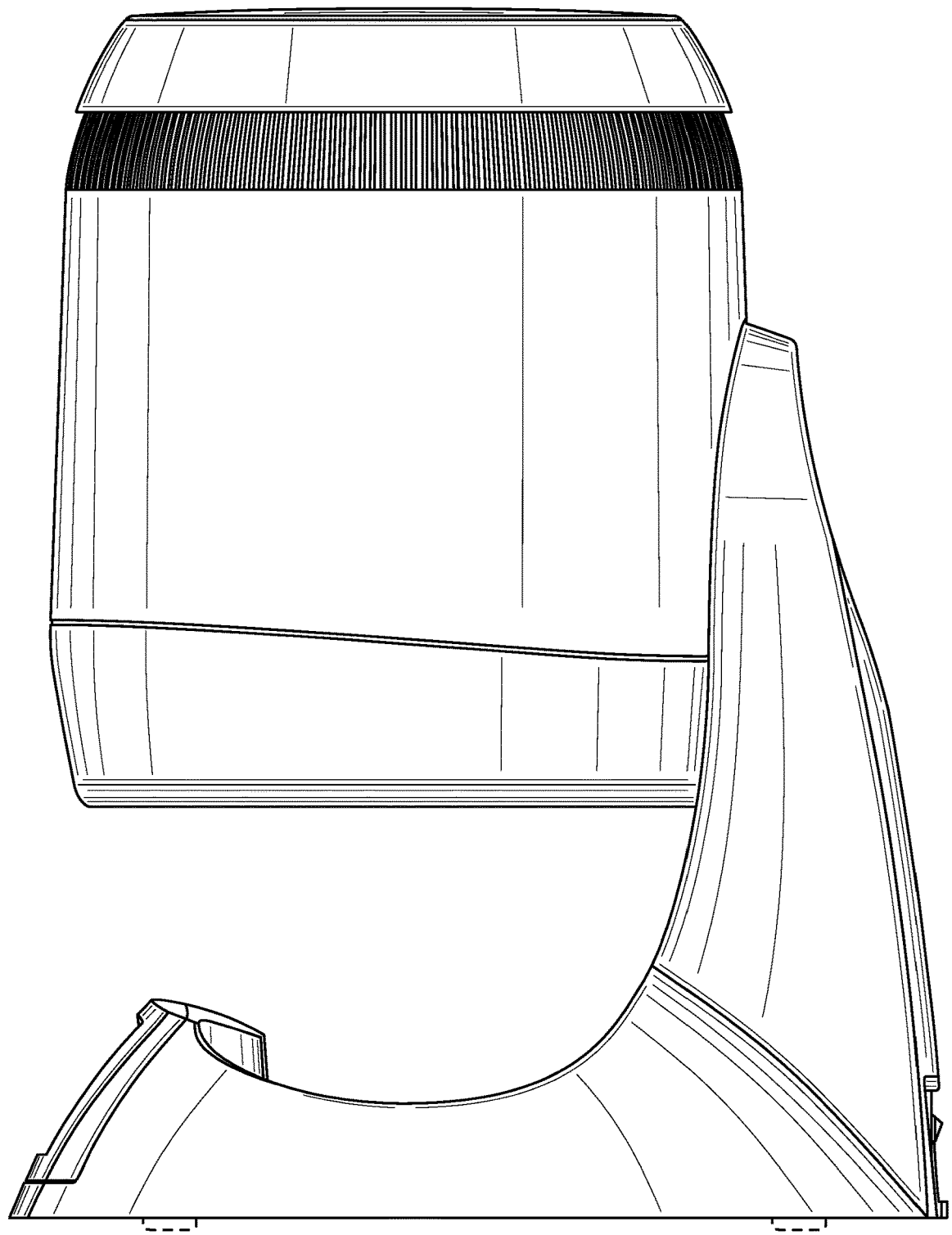
Figure 2A:
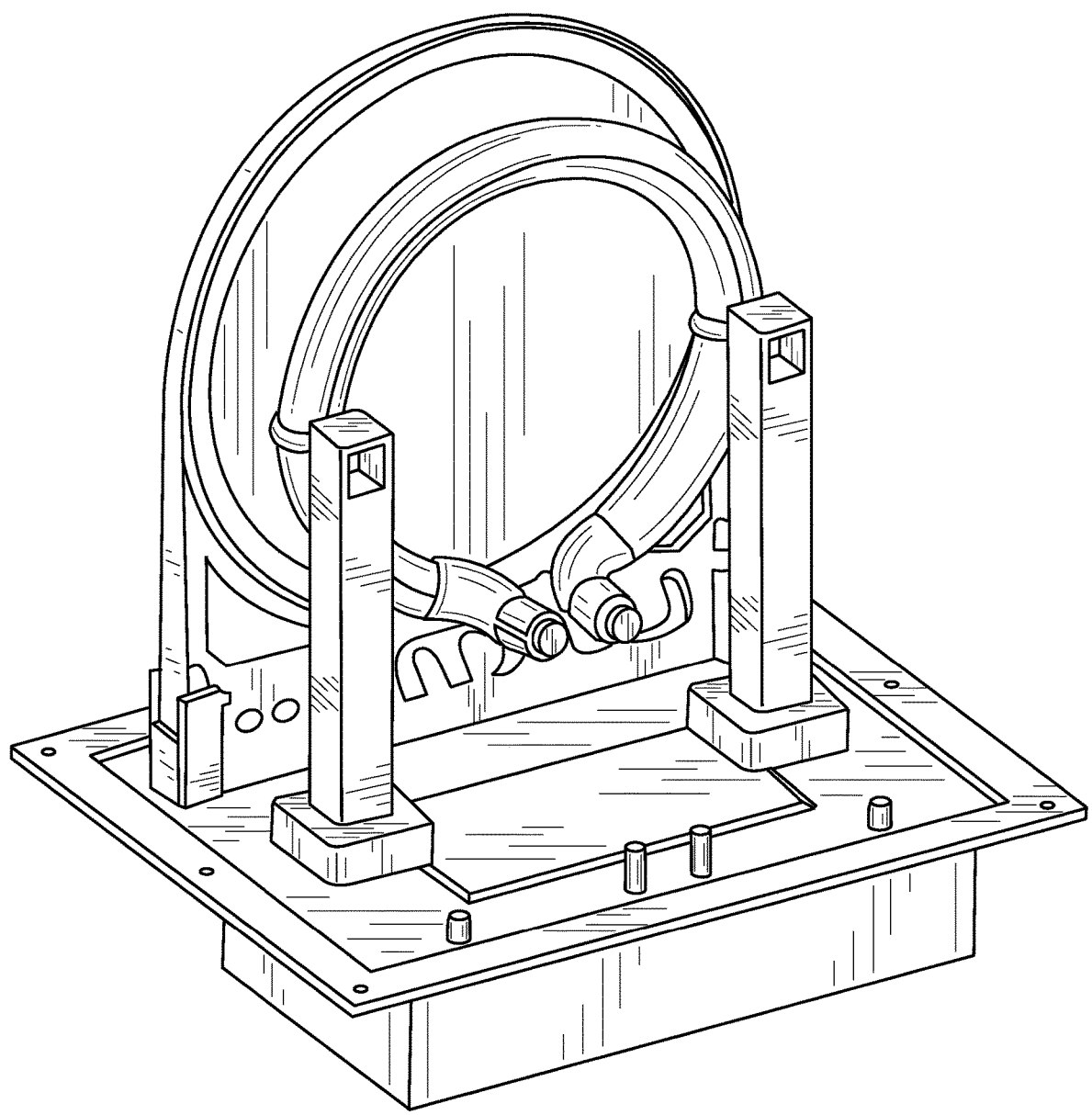
FIGS. 2A-D illustrate an exemplary device for installation into a heating, ventilation, and air conditioning (HVAC) system to provide PHPG that is substantially free of hydration and ozone PHPG to an environment according to the present disclosure.
Figure 2B:
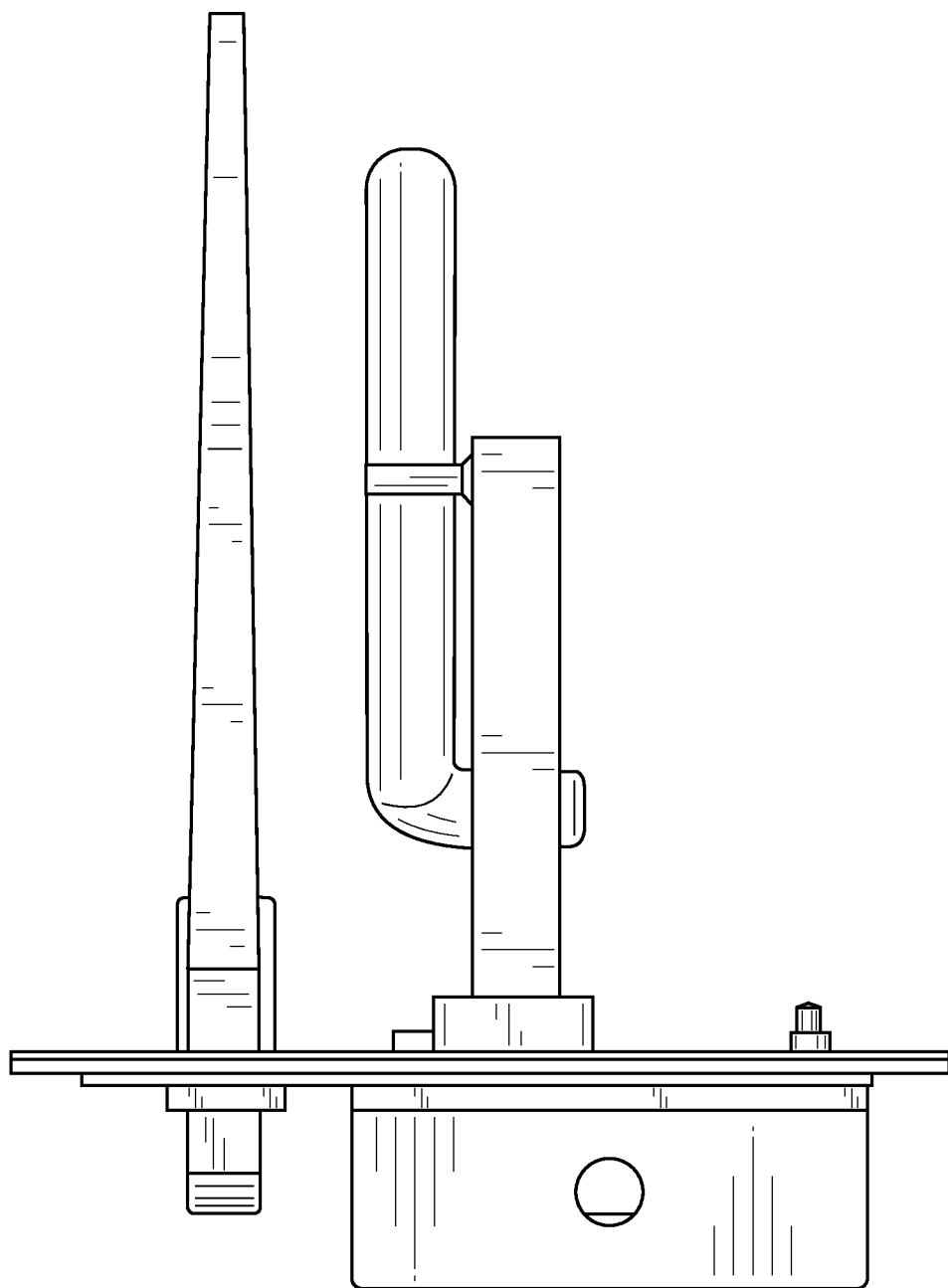
Figure 2C:
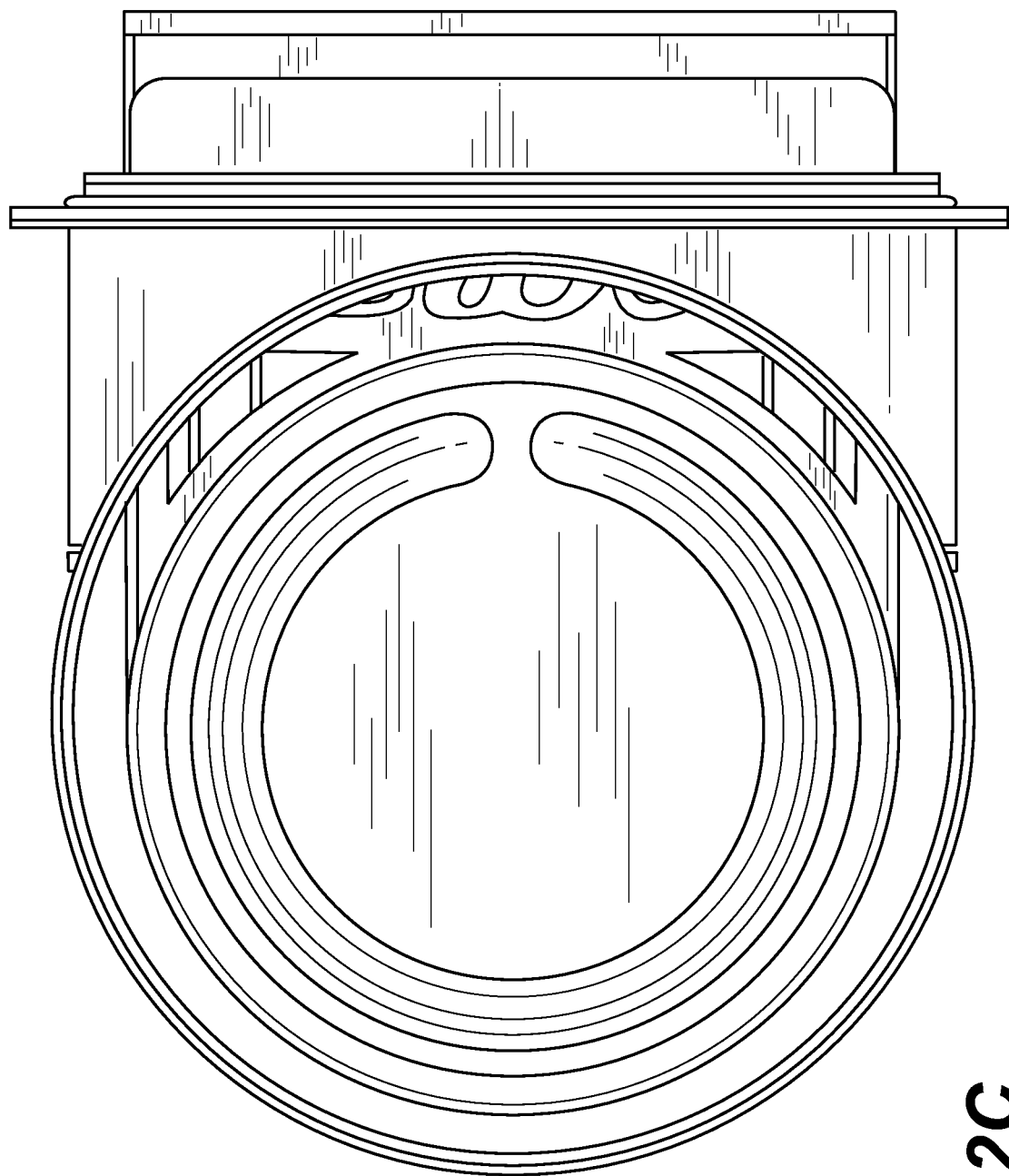
Figure 2D:
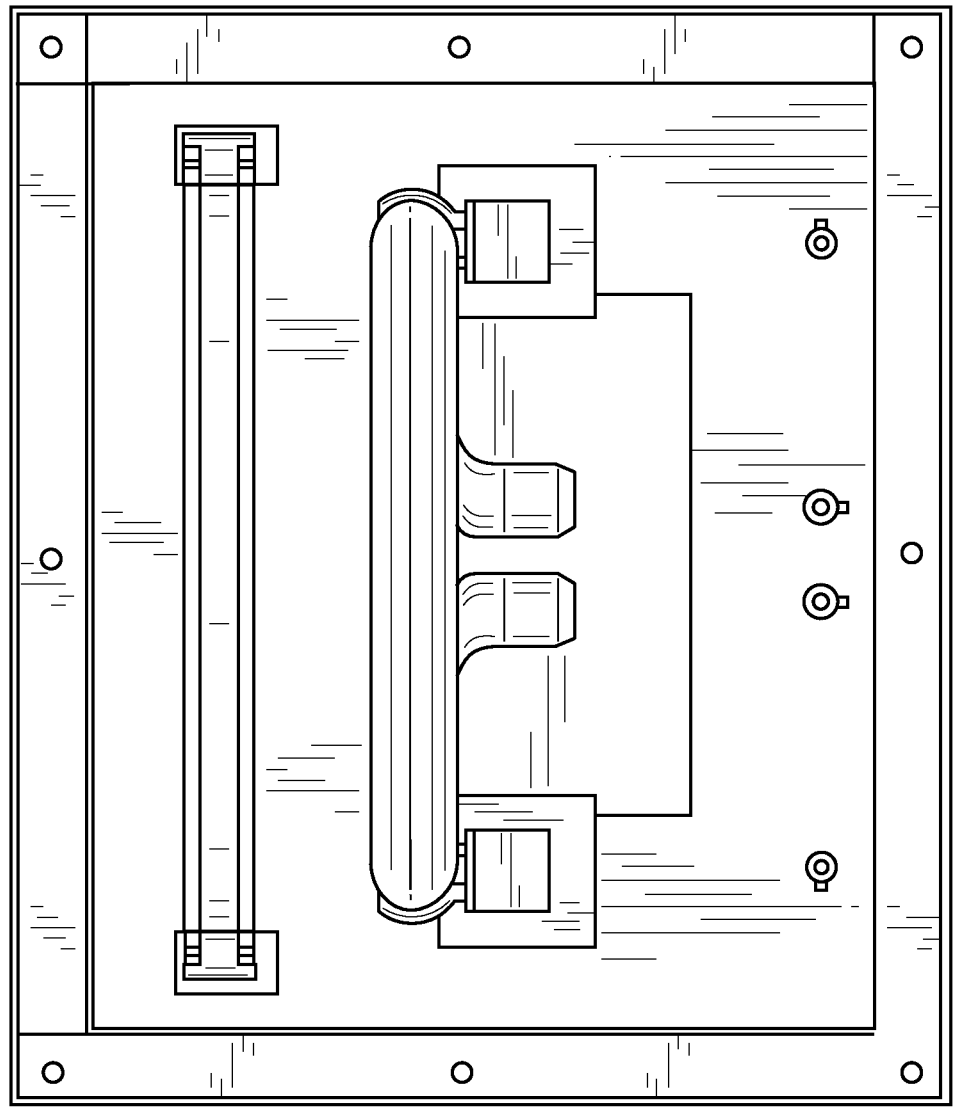
Figure 2E:
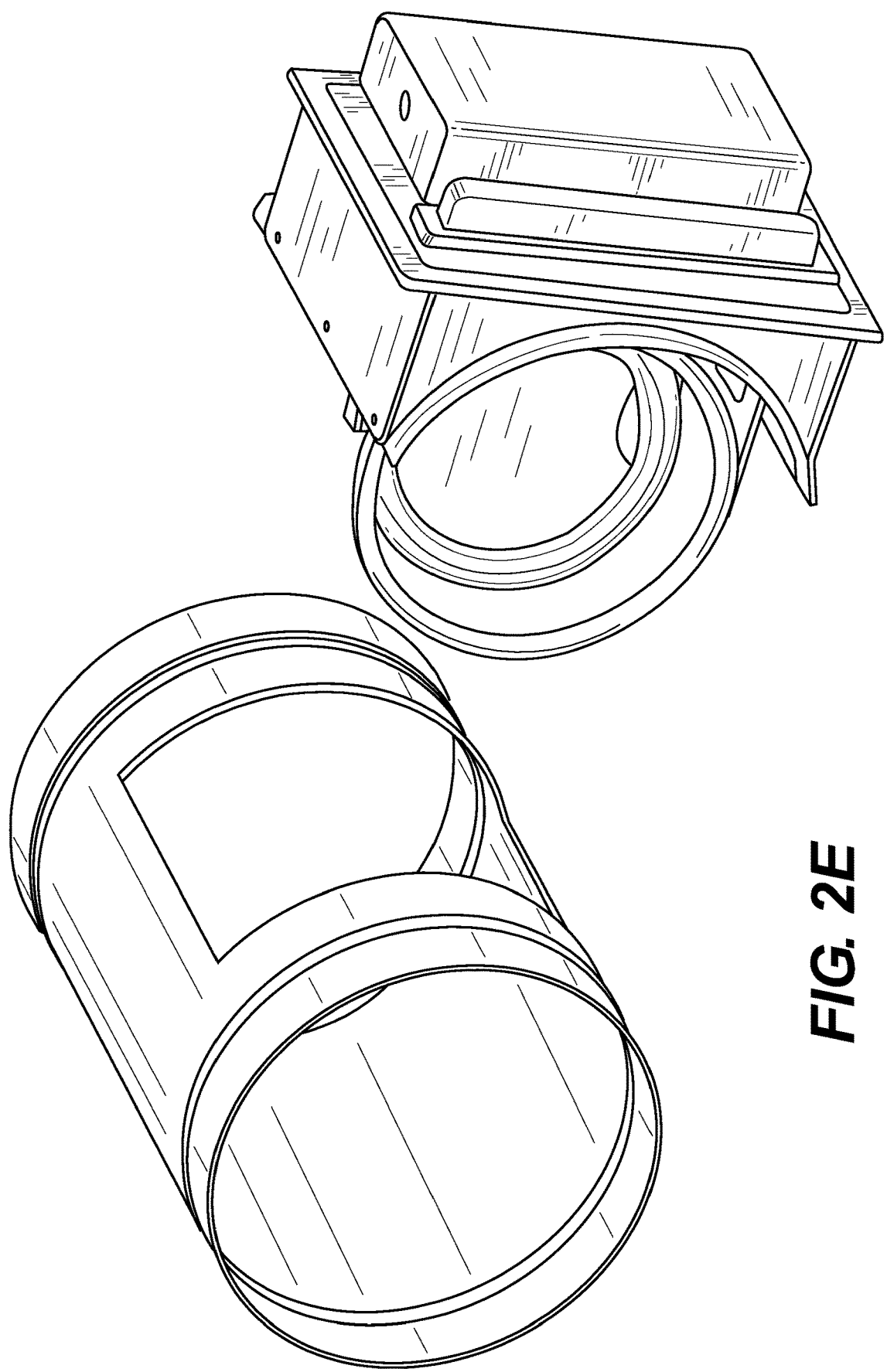
FIG. 2E illustrates a view of an exemplary HVAC device and a target duct adapted for installation.

As used herein, hydrogen peroxide is provided as a purified hydrogen peroxide gas (PHPG) and is alternatively described in the present disclosure as a near-ideal gas phase hydrogen peroxide, or non-hydrated hydrogen peroxide gas. Purified Hydrogen Peroxide gas is gaseous hydrogen peroxide ($H_2O_2$) that is substantially free of at least hydration (in the form of $H_2O_2$ in solution) and substantially free of ozone. As used herein, purified hydrogen peroxide gas (PHPG) is not condensed or present as a droplet. Purified hydrogen peroxide gas (PHPG) is produced as a gas phase free of hydration or water molecules bonded by covalence, van der Waals forces, or London forces and is substantially free of ozone. Devices suitable for the production of PHPG for use according the present disclosure generate PHPG that is non-hydrated and free of ozone. In this form hydrogen peroxide (e.g., PHPG) behaves, in all respects, as a near-ideal gas and is not hydrated, or otherwise combined with water when produced. As used in the present disclosure, PHPG is distinguishable from aerosolized aqueous hydrogen peroxide as PHPG is not hydrated, non-toxic and the $H_2O_2$ molecules are present in much lower concentrations. In contrast, aerosolized aqueous hydrogen peroxide, commonly referred to as vaporized hydrogen peroxide (VHP) consists of micro-droplets. Aerosolized or vaporized hydrogen peroxide is an EPA registered pesticide (EPA PC Code #000595).

A suitable diffuser device may be used to generate the PHPG, such as those disclosed in WO/2009/021108 or WO/2010/093796, the contents of which are herein incorporated by reference. The diffuser design may optimize PHPG production by spreading the air permeable photocatalytic PHPG reactor surface thinly over a large area that is perpendicular to air flow (e.g., in certain aspects, over a sail-like area), rather than by compacting it into a volume-optimizing morphology designed to maximize residence time within the plasma reactor.

In accordance with the present disclosure, the terms "substantial absence of ozone," "substantially free of ozone," etc., generally mean amounts of ozone below about 0.015 ppm, down to levels below the LOD (level of detection) for ozone. As used herein, "free of ozone" means free of detectable levels of ozone when the peroxide gas is produced. Such levels are below the generally accepted limits for human health. In this regard, the Food and Drug Administration (FDA) requires ozone output of indoor medical devices to be no more than 0.05 ppm of ozone. The Occupational Safety and Health Administration (OSHA) requires that workers not be exposed to an average concentration of more than 0.10 ppm of ozone for 8 hours. The National Institute of Occupational Safety and Health (NIOSH) recommends an upper limit of 0.10 ppm of ozone, not to be exceeded at any time. EPA's National Ambient Air Quality Standard for ozone is a maximum 8 hour average outdoor concentration of 0.08 ppm. Diffuser devices suitable for preparing PHPG for the methods of the present disclosure have consistently demonstrated that they do not produce ozone at levels detectable by means of a Draeger Tube.

PHPG is not appreciably lighter or heavier than air, having a molar mass of 34.0148 grams per mole. In this form, gas phase hydrogen peroxide can penetrate to any space that can be reached by air itself. This includes all areas, such as crevices between materials, inside air-permeable cushions and in air-permeable bedding. Gas phase hydrogen peroxide diffuses through air as any other gas would, and passes through air permeable materials, unhindered by the surface tension of water as is seen in the behavior of micro-droplets comprising aqueous phase vapor forms of hydrogen peroxide (e.g., VHP) often referred to as gaseous. Whatever else micro-droplets of hydrogen peroxide or VHP may be, they are not gaseous and do not behave as a gas. Aerosolized micro-droplets of hydrogen peroxide are toxic and are not suitable for the methods and enclosed habitable spaces of the present disclosure.

Continuously produced via a hydrogen peroxide diffuser device, for example as provided in U.S. Pat. No. 8,168,122, issued May 1, 2012, and U.S. Pat. No. 8,685,329, issued Apr. 1, 2014, an equilibrium concentration above 0.01 parts per million of gas phase hydrogen peroxide may be achieved and maintained continuously in an enclosed space or environment. At equilibrium, at one atmosphere pressure, and at 19.51 degrees Celsius, gas phase hydrogen peroxide will be present in every cubic micron of air at an average amount of one molecule per cubic micron for each 0.04 parts per million of concentration. At one part per million, the average number of hydrogen peroxide molecules per cubic micron will be 25 and at 3.2 parts per million it will be 80.

As used herein, the PHPG becomes distributed homogeneously in an enclosed space or environment. The homogenous distribution of the PHPG in an enclosed space or environment maximizes the surface area of the lungs exposed to PHPG. In contrast, aerosolized hydrogen peroxide (or vaporized hydrogen peroxide (VHP)) is distributed non-homogenously due to the high levels of hydrogen peroxide present in each micro-droplet.

As used herein, the term "enclosed space," "closed space," or "closed environment" means any space that is substantially separated from exchanging air with the outside. A closed space need not be completely closed to the outside, but rather should be sufficiently closed to enable the atmosphere within the closed space to be controlled reliably. In certain aspects, an enclosed space may be provided inside another enclosed space, for example as an isolated room, or a cage or enclosure in a facility; this term includes, for example, rooms, buildings, cages, livestock confinements or any space wherein the air is not freely exchangeable. Enclosed spaces according to the present disclosure are not limited to a specific size. In certain aspects, an enclosed space is a habitable space, such as a house, apartment, hotel, motel, airplane, spacecraft, restaurant, fitness center, health bar, or other buildings. In certain aspects, an enclosed space comprises a large space, including but not limited to auditoriums, exposition centers, and stadiums. In other aspects, an enclosed space includes rooms for sleeping, resting or exercising, e.g. a gym. It is to be understood that an "enclosed space" as described herein may include locations at sea or under water. For example, an enclosure may be part of a boat or submarine. In one aspect, the methods provided herein may improve the air quality or reduce the transmission of illness on a submarine. In another example, the methods provided herein may reduce the transmission of a respiratory infection or control a pathogen on a cruise ship. In yet another aspect, the enclosure may be on a spaceship, spacecraft, or space station. In some aspects, the enclosed spaces include control of such environment conditions including, but not limited to, temperature and humidity.

The ability to reliably control the atmosphere in an enclosed space depends on the air exchange rate with the outdoors and is an important factor in determining the steady state level PHPG gas. The air exchange rate is affected by the design, construction, and operating parameters of buildings and is ultimately a function of infiltration (air that flows into structures through openings, joints, and cracks in walls, floors, and ceilings and around windows and doors), natural ventilation (air that flows through opened windows and doors), and mechanical ventilation (air that is forced indoors or vented outdoors by ventilation devices, such as fans or air handling systems). Outdoor climate and weather conditions combined with occupant behavior can also affect indoor air quality and the ability to control the environment in an enclosed space.

As used throughout, a "subject" means an individual vertebrate animal. Thus, the "subject" can include, but is not limited to, mammals, birds, reptiles and amphibians. "Subject" includes humans and other primates, domesticated animals (e.g., cats, dogs, etc.), livestock (e.g., cattle, horses, poultry, pigs, sheep, goats, etc.), zoo animals, and laboratory animals (e.g., mice, rabbits, rats, guinea pigs, monkeys, etc.). In certain aspects, the subject is a human. As used herein, subjects are not invertebrates and unicellular organisms.

As used herein, the singular forms "a," "an" and "the" include plural references unless the context clearly dictates otherwise. For example, the term "a subject" or "at least one subject" may include a plurality of subjects, including mixtures thereof. Also as used herein, a subject includes and provides for a population of subjects. As used herein, a population of subjects may further include a mixed population of subjects including for example mixed populations of animals (e.g. a zoo or animal facility).

In aspects according the present disclosure, methods for controlling, treating, or mitigating a respiratory illness, infection, or condition may be measured by comparing a population of subjects exposed to PHPG to a comparable population of subjects not exposed to PHPG. Comparison of populations allows for a statistical analysis using methods known in the art to identify and quantify changes in the number or extent of respiratory illness, infection or condition. In one aspect, the population may be selected from the group consisting of a human, laboratory animals, housepets, or livestock animals. For example, a select population may be comprised of healthy individuals. "Healthy," as used herein, means individuals without indications or symptoms of the presence of a pulmonary disease, infection, or condition. In one aspect, a population may be a family living in a house having an environment including PHPG compared to similar families that are not exposed to PHPG. In another aspect, populations may comprise treated or untreated subjects exposed to a hospital, veterinary hospital, quarantine area, house, apartment, hotel, airplane, spacecraft, fitness center, restaurant, health bar, or the like. In certain aspects, the population of PHPG treated individuals may be selected and compared to a population of individuals having similar occupations, living conditions, ethnic and economic backgrounds, or combinations thereof. In an aspect, subject populations may be medical and veterinary practitioners. Methods for selecting populations for epidemiological studies are known in the art.

In aspects according to the present disclosure, a population may be compared by determining the number and extent of respiratory illness in a comparable time period before and after exposure to a PHPG environment. In one aspect, the effects of PHPG exposure is compared on a year-to-year basis. In other aspects, the effects of PHPG treatment in a population can be determined from a multi-year analysis.

In an aspect according the present disclosure, the benefit of PHPG treatment may be determined in animal populations, including for example, laboratory animal populations. By comparing the percentage requiring veterinary intervention in treated and untreated populations, the benefits of PHPG treatment may demonstrated and quantified. In an aspect, treatment with PHPG reduces veterinary intervention by at least 10% over untreated control populations. In another aspect, PHPG reduces veterinary intervention by at least 20% over untreated control populations. In yet another aspect, PHPG reduces veterinary intervention by at least 30% or 40% over untreated control populations. In some aspects, the experimental populations are compared over a one month period. In other aspects, experimental populations are compared over a two month period. In further aspects, experimental populations are compared over a 6 month, 7 month, 8 month, 9 month, 10 month, 11 month, or one year period.

In one aspect, the benefit of exposure to an environment having PHPG may be determined by comparing the percentages of people in treated and untreated populations requiring medical intervention. In some aspects, medical intervention may include visiting a doctor, obtaining and using a prescription medicament, or self-medicating with non-prescription medicament. In one aspect, treatment with PHPG may reduce medical intervention by at least 10%. In another aspect, the percentage of people requiring medical intervention is reduced by at least 15%. In another aspect, the percentage of people requiring medical intervention is reduced by at least 20% or 25%. In yet other aspects, the percentage of people requiring medical intervention is reduced by at least, 30%, 35% , 40%, or 50% or more.

In aspects according to the present disclosure, treatment of a population with PHPG results in a decrease in the number of sick days claimed. In certain aspects, the number of sick days is reduced by 10% or more. In other aspects, the number of sick days taken by a population of people is reduced by 20% or more. In further aspects, the number of missed days due to sickness may be reduced by 30% or more. In other aspects, an individual in a treated population may reduce the number of sick days claimed per year by at least 1, on average. In another aspect, an individual in a treated population may take 2 or 3 fewer sick days per year using the treatment methods of the present disclosure. In further aspects, the number of sick days may be reduced by 5 or more per year.

In some aspects, the benefit of exposure to an environment having PHPG may be determined by comparing the number of sick days taken by people exposed to PHPG to the number of sick days taken by people not exposed to PHPG over a period of time. In some aspects, the period of time is one month. In other aspects, the period of time is 6 months, 7 months, 8 months, 9 months, 10 months, 11 months, or one year. In one aspect, the number of sick days in a population of people exposed to PHPG as described herein is reduced by at least 10% as compared to the number of sick days taken in a population of people not exposed to PHPG. In yet another aspect, the number of sick days is reduce by at least 15%, 20%, 25%, 30%, 35% , 40%, or 50% compared to the number of sick days taken in a population of people not exposed to PHPG.

In aspects according the present disclosure, the beneficial effects of exposure of a subject to PHPG environments do not require continuous exposure. Significantly, continuous exposure has no adverse effects on a subject. Surprisingly, the beneficial effects of exposure to a PHPG containing environment persist in a subject, even though the subject is not exposed continuously throughout the day or even for a majority of the day. Not to be limited by theory, it is thought that PHPG increases or enhances the body's innate defenses to various pathogens through the production of isothiocyanate. In addition, PHPG may provide benefits during preclinical disease incubation periods thereby avoiding symptomatic infection. Thus, subjects benefit not only from the decrease in pathogens in the PHPG containing environment (PHPG acts as a direct bactericidal, virucidal, and fungicidal agent) but also benefit when they leave the PHPG environment.

As used herein, "a reduction in the severity," or "reducing the severity" means in the length of time that symptoms are evident or a reduction in the severity of the symptoms. In some aspects, a reduction in the severity includes a reduced need for palliative medicines such as decongestants and antihistamines. A reduction of the severity of respiratory infections is associated with reduced nasal congestion, runny nose (rhinorrhea), nasal discharge, nasal breathing, sneezing, sore or scratchy throat, painful swallowing (odynophagia), cough, malaise, or fever (more common in children). Reductions may be exhibited by decreases in the length of time of illness or a reduction in the number or quality of the symptoms. Reductions in severity may also be evident by reduced absences from work or school and faster returns to normal activities. Respiratory infections typically last between 3 and 14 days and reductions in severity may include decreases in the length of time to less than one day, less than two days, or less than 3 days.

As used herein, "reduced transmission" or "prevented transmission" of a respiratory infection means a reduced incidence of infectious disease in subjects exposed to an infectious respiratory disease. Reduced transmission may be measured in population surveys comparing PHPG treated and non-treated subjects. Reduced transmission may also be identified by a decrease in the number or extent of respiratory infection of a subject over the course of a year or over the course of the "flu" season.

As used herein, "improved lung function" means that the subject has improved or increased static lung volume, increased total lung capacity, increased partial pressure of oxygen in arterial blood gases, decreased residual volume or combinations thereof. Improved lung function may be measured after extended exposure to a PHPG containing environment.

As used herein, "prophylaxis" means that exposure to PHPG containing environments improves or increases the ability of the subject to resist respiratory illness, generally before exposure to an infectious agent or in anticipation of exposure. In certain aspects, exposure to PHPG containing environments is initiated in anticipation of some future exposure to a known pathogen. As used herein, improving the health of a subject by prophylaxis includes enhancing a subject's host defenses to a respiratory infection, stimulating a subject's defenses to a respiratory infection, increasing the concentration of hypothiocyanate ion in a respiratory system, increasing the rate of hypothiocyanate ion production catalyzed by lactoperoxidase (LPO), preventing a respiratory infection, reducing the transmission of a respiratory infection, preventing a respiratory illness, preparing an environment suitable for occupancy, and combinations thereof.

Not to be limited by theory, gas phase hydrogen peroxide will be "inhaled" or processed by subjects including animals having lungs including mammals, birds, reptiles and amphibians. As used herein, suitable subjects include domesticated animals (e.g., cats, dogs, etc.), livestock (e.g., cattle, horses, poultry, pigs, sheep, goats, etc.), zoo animals, and laboratory animals (e.g., mouse, rabbit, rat, guinea pig, etc.). In one aspect, the subject is a mammal, such as a primate or a human.

Non arthropod animals such as humans and other vertebrates have respiratory mechanisms that protect them from equivalent concentrations of gas phase hydrogen peroxide. Human lungs produce hydrogen peroxide at high rates and a cubic micron of human lung secretion contains an equilibrium concentration of between 600 molecules, and 60,000 molecules of hydrogen peroxide in aqueous phase, along with enzymes that consume hydrogen peroxide and regulate its concentration. Enzymes such as lactoperoxidase and catalase which perform this function are known to have enzymatic velocities of thousands of molecular reactions per second.

As provided by the methods of the present disclosure, prophylaxis is indicated for example, in anticipation of possible exposure to influenza virus during flu season or during outbreaks of other viral diseases, including but not limited to influenza virus, severe acute respiratory syndrome (SARS), Middle East Respiratory Syndrome (MERS), ebola, porcine reproductive and respiratory syndrome virus (PRRSV) infection, and respiratory syncytial virus (RSV). In other aspects, prophylaxis by exposure to PHPG containing environments includes pretreatment of a subject in anticipation of exposure to fungal and mold pathogens, including without limitation, *Aspergillus* spp., *Candida albicans, Sclerotinia* or *Pneumocystis* spp. Prophylaxis includes in certain aspects, treatment of a subject in a PHPG containing environment to prevent infection by bacteria including, without limitation, *Mycoplasma* sp, including *Mycoplasma pneumonia, Mycobacterium tuberculosis, Acinetobacter* sp., *Chlamydophila* sp., *Streptococcus* sp., *Haemophilus* sp., or *Staphylococcus* spp. In certain aspects, prophylaxis includes concurrent treatment with PHPG of an existing respiratory illness. In certain other aspects, methods of prophylaxis comprising exposing a subject to PHPG gas may further be used for treatment of infection.

PHPG levels as low as 0.01 ppm are sufficient to provide a prophylactic effect according to the present disclosure in a subject exposed for at least 4 hours daily. In other aspects, a PHPG level of at least 0.05 ppm for at least 4 hours provides prophylaxis. In yet another aspect, a PHPG level of 0.1 ppm for at least 4 hours provides prophylaxis. In yet another aspect, a PHPG level of at least 0.2 or 0.3 ppm for at least 4 hours provides prophylaxis. In certain aspects, exposure of a subject to between 0.01 and 1 ppm for at least 4 hours provides prophylaxis. In other aspects a suitable range of PHPG for prophylaxis may be between 0.1 and 7 ppm, for at least 4 hours per day. In an aspect, a subject may be exposed to between 0.2 to 2 ppm for 4 hours per day.

As used herein improving the health of a subject by mitigation includes enhancing a host's deference to a respiratory infection; stimulating a host's defenses to a respiratory infection; increasing the concentration of hypothiocyanate ion in a respiratory system; increasing the rate of hypothiocyanate ion production catalyzed by lactoperoxidase (LPO); reducing the severity of a respiratory infection; controlling a pathogen in the respiratory system; managing a condition affecting the lungs; decreasing the length of time of a respiratory infection; improving the lung function; preventing, treating, controlling a respiratory illness; reducing the transmission of a respiratory infection; preventing a respiratory illness; preparing an environment suitable for occupancy.

PHPG levels as low as 0.01 ppm are sufficient to provide a mitigation effect according to the present disclosure in a subject exposed for at least 4 hours daily. In other aspects, a PHPG level of at least 0.05 ppm for at least 4 hours provides mitigation. In yet another aspect, a PHPG level of 0.1 ppm for at least 4 hours provides mitigation. In yet another aspect, a PHPG level of at least 0.2 or 0.3 ppm for at least 4 hours provides mitigation. In certain aspects, exposure of a subject to between 0.01 and 1 ppm for at least 4 hours provides mitigation. In other aspects a suitable range of PHPG for mitigation may be between 0.1 and 7 ppm for at least 4 hours per day. In an aspect, a subject may be exposed to between 0.2 to 2 ppm for 4 hours per day.

As used herein treatment of a medical condition includes enhancing a host's deference to a respiratory infection; stimulating a host's defenses to a respiratory infection; increasing the concentration of hypothiocyanate ion in a respiratory system; increasing the rate of hypothiocyanate ion production catalyzed by lactoperoxidase (LPO); reducing the severity of a respiratory infection; controlling a pathogen in the respiratory system; managing a condition affecting the lungs; decreasing the severity of a respiratory infection; improving the lung function; preventing, treating, or controlling a respiratory illness.

The present disclosure provides for, and includes, enclosed spaces for human or veterinary use comprising purified hydrogen peroxide gas (PHPG) at a steady state concentration of at least 0.01 parts per million wherein said PHPG is free of hydration and ozone. In another aspect, enclosed spaces for human or veterinary use comprise purified hydrogen peroxide gas (PHPG) at a steady state concentration of at least 0.05 parts per million wherein the PHPG is free of hydration and ozone. As provided herein, exposure of subjects to enclosed spaces having PHPG provides for improved respiratory system function and health.

The present disclosure further provides for, and includes, and enclosed space that is a dwelling comprising purified hydrogen peroxide gas (PHPG) at a steady state concentration of at least 0.01 parts per million wherein the PHPG is free of hydration and ozone. In another aspect, a dwelling comprises purified hydrogen peroxide gas (PHPG) at a steady state concentration of at least 0.05 parts per million wherein the PHPG is free of hydration and ozone. As used herein, a "dwelling," is a self-contained unit of accommodation including a building, a part of a building a caravan, houseboat, mobile home, manufactured home, used and occupied for subject habitation or intended to be used and occupied by a subject. In an aspect, the subject that uses and occupies a dwelling is human. In another aspect, a subject that uses and occupies a dwelling is an animal. In certain aspects, enclosed spaces that are dwellings include hospitals, veterinary hospitals, quarantine areas, houses, apartments, airplanes, spacecraft, hotels, and motels. As used herein, a dwelling need not be continuously occupied and may be for temporary use. Examples of dwellings for temporary use include tents and other structures prepared for example, to accommodate subjects during emergencies.

The ability to maintain a PHPG concentration at desired levels depends on the rate of production of PHPG and the volume of the space and the ability to control the rate of loss. The rate of loss is, in turn, determined by the spontaneous decay of peroxide, the reaction with pathogens and compounds and by the loss of peroxide through exchange with the outside air. Accordingly, the steady state level of PHPG can be increased by increasing the rate of production and by further isolating the exchange of air of the enclosed space with the outside air.

In an aspect according to the present disclosure, the steady state level of an enclosed for human or veterinary use comprises purified hydrogen peroxide gas (PHPG) at a steady state concentration of at least 0.05 parts per million. In an aspect according to the present disclosure, the steady state level of an enclosed for human or veterinary comprises purified hydrogen peroxide gas (PHPG) at a steady state concentration of at least 0.01 parts per million. In another aspect, the steady state amount of purified hydrogen peroxide gas may vary from about 0.005 ppm to about 0.10 ppm, more particularly, from about 0.02 ppm to about 0.05 ppm, in the environment. In certain aspects, the steady state amount of purified hydrogen peroxide gas (PHPG) may vary from about 0.005 ppm to about 0.40 ppm. More particularly, steady state purified hydrogen peroxide gas (PHPG) levels from about 0.02 ppm to about 7 ppm can be produced in the environment to be treated.

The present disclosure further provides and relates generally to methods for the increase of the hypothiocyanate ion in mammalian lungs and devices related thereto. In certain aspects, electro-catalytic processes may be utilized to form gas phase hydrogen peroxide for use in the methods and devices described herein.

Gas phase hydrogen peroxide will be inhaled by subjects in the habitable enclosed space or environment created according to the methods of the present disclosure or can be directly supplied to the lungs by devices. As discussed above, humans and other vertebrates have respiratory mechanisms that consume and use equivalent concentrations of hydrogen peroxide. For example, human lungs produce hydrogen peroxide at high rates, and a cubic micron of human lung secretion contains an equilibrium concentration of between 600 and 60,000 molecules of hydrogen peroxide in aqueous phase, along with enzymes that consume hydrogen peroxide and regulate its concentration. Enzymes such as lactoperoxidase and catalase which perform this function are known to have enzymatic velocities of thousands of molecular reactions per second.

Not to be limited by theory, once inhaled, the hydrogen peroxide gas is absorbed by the aqueous secretions of the respiratory system and used by lactoperoxidase, catalase, and other enzymes to produce hypothiocyanate ions from thiocyanate ions in mammalian lungs by means of the following reaction:

$$SCN^- + H_2O_2 \rightarrow OSCN^- + H_2O$$

In one aspect of the disclosure, a method of increasing hypothiocyanate ion production in human lungs is disclosed. The method generally comprises (a) generating a gas comprised of hydrogen peroxide gas that is substantially free of, e.g., hydration (i.e., non-hydrated, in the form of water in solution or water molecules bonded by covalence, van der Waals forces, or London forces), ozone, plasma species, and/or organic species; and (b) directing the gas comprised of hydrogen peroxide into the environment or directly to the lungs where it can be inhaled such that the hydrogen peroxide interacts with enzymes in the lungs to increase the concentration of hypothiocyanate ions in the lungs.

In other aspects, a method of increasing hypothiocyanate ion production in non-human lungs is disclosed. The method generally comprises (a) generating a gas comprised of hydrogen peroxide gas that is substantially free of, e.g., hydration (i.e., non-hydrated, in the form of water in solution or water molecules bonded by covalence, van der Waals forces, or London forces), ozone, plasma species, and/or organic species; and (b) directing the gas comprised of hydrogen peroxide into the environment or directly to the lungs where it can be inhaled such that the hydrogen peroxide interacts with enzymes in the lungs to increase the concentration of hypothiocyanate ions in the lungs.

In a number of aspects, methods for increasing hypothiocyanate ion production in human lungs includes exposing a human to an environment having PHPG at a final concentration of at least 0.01 ppm. In an aspect, the concentration of PHPG may be at least 0.05 ppm. In an aspect, the concentration of PHPG may be at least 0.1 ppm. In another aspect, PHPG concentration may be 0.2 ppm. In yet another aspect, the PHPG concentration may be 0.25 ppm. In an aspect, the concentration of PHPG may be at least 0.4 ppm or 0.5 ppm. In an aspect, the concentration of PHPG may be at least 0.6 or 0.7 ppm. In another aspect, PHPG concentration may be up to 1.0 ppm. In yet another aspect, the PHPG concentration may be between 0.1 and 7.0 ppm.

In a number of aspects, hypothiocyanate ion production may be increased by exposing a subject, such as an animal or human, continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 0.5 ppm PHPG for at least 4 hours. In an aspect, the subject may be exposed to environment comprising at least 0.5 ppm PHPG 2, 3, 4, 5, 6, or more times in a 7 day period. In other aspects, exposing a subject to PHPG may be repeated regularly as a prophylactic measure.

In certain aspects, the method comprises producing purified hydrogen peroxide gas (PHPG) and directing the Hydrogen Peroxide Gas into the environment or directly to the lungs such that the Hydrogen Peroxide Gas can be breathed and increase the hypothiocyanate ion concentration in the lungs.

The present disclosure provides for, and includes, methods for improving the health of a subject including prophylaxis, mitigation, or treatment of a medical condition by exposing a subject to an enclosed space having an environment having PHPG at concentration of at least 0.01 parts per million (ppm). In certain aspects, methods for improving the health of a subject include prophylaxis, mitigation, or treatment of a medical condition include exposing a subject to PHPG levels of at least 0.05 ppm. In yet other aspects, PHPG levels may be significantly increased up to 7 ppm, for example during emergencies, including outbreaks and epidemics of infectious disease.

The present disclosure provides for, and includes, methods for improving air quality in an enclosed space comprising introducing purified hydrogen peroxide gas (PHPG) concentration of at least 0.01 parts per million where the PHPG free of hydration and ozone and wherein the air stream is introduced from an indoor air recirculation stream. In another aspect, the PHPG concentration is at least 0.05 ppm. In other aspects, the PHPG is introduced to the enclosed space using a standalone PHPG producing device.

In a number of aspects, air quality may be improved by introducing PHPG into an enclosed space and maintaining a concentration of PHPG ranging between 0.01 and 7.0 ppm. In certain aspects, the PHPG may be maintained at a concentration above 0.2 ppm. In yet another aspect, the PHPG may be maintained at a concentration above 0.25 ppm. In an aspect, the concentration of PHPG may be at least 0.4 ppm or 0.5 ppm. In an aspect, the concentration of PHPG may be at least 0.6 or 0.7 ppm. In another aspect, PHPG concentration may be up to 1.0 ppm. In yet another aspect, the PHPG concentration may be between 0.1 and 7.0 ppm. In certain aspects, the air quality is improved by maintaining the PHPG in the enclosed space for at least 1 hour per day. In other aspects, the air quality is improved by maintaining the PHPG in the enclosed space for at least 4 hours per day.

In aspects according the present disclosure, the PHPG is provided to an enclosed space at a final concentration of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, least 0.6 ppm, least 0.7 ppm, least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm.

The present disclosure provides for, and includes, methods for preparing a purified hydrogen peroxide gas (PHPG) containing environment comprising generating PHPG that is free of hydration and ozone, and accumulating said PHPG until a final concentration of at least 0.01 parts per million (ppm) is achieved. In another aspect, the final concentration of PHPG is at least 0.05 ppm.

The present disclosure provides for, and includes, methods for providing an enclosed space comprising a purified hydrogen peroxide gas (PHPG) comprising providing PHPG that is free of hydration and ozone to the environment at a rate sufficient to maintain PHPG gas at a final concentration of at least 0.01 parts per million (ppm). In another aspect, the enclosed space achieves a PHPG concentration of at least 0.05 ppm The present disclosure provides for, and includes, a method of treatment comprising providing a treatment environment comprising an enclosed space suitable for habitation wherein said treatment environment comprises a purified hydrogen peroxide gas (PHPG) concentration of at least 0.01 parts per million and the PHPG is free of hydration and ozone; exposing a subject in need of treatment to the treatment environment for a treatment period. In another aspect, the method of treatment comprises providing a treatment environment comprising an enclosed space suitable for habitation wherein the treatment environment comprises a purified hydrogen peroxide gas (PHPG) concentration of at least 0.05 parts per million and the PHPG is free of hydration and ozone; exposing a subject in need of treatment to the treatment environment for a treatment period.

The present disclosure provides for, and includes, methods for increasing or improving host defenses to a respiratory infection of a subject comprising providing an environment comprising a purified hydrogen peroxide gas (PHPG) that is free of hydration and ozone at a final concentration of at least 0.01 parts per million; and exposing the subject to the environment for one or more periods of time, thereby increasing the level of hypothiocyanate ion in the lungs of the subject. In other aspects, the final steady state concentration is at least 0.05 ppm PHPG.

The present disclosure provides for, and includes, methods for treating a respiratory illness in a subject comprising providing an environment comprising a purified hydrogen peroxide gas (PHPG) that is free of hydration and ozone at a final concentration of at least 0.01 parts per million (ppm); and exposing the subject to the environment for at least one period of time, wherein the treating comprises reducing the severity of a respiratory infection, reducing the duration of a respiratory infection, reducing the severity of an allergy, preventing transmission of a respiratory infection, reducing transmission of a respiratory infection in a population, improving lung function, or any combination thereof. In another aspect, methods for treating a respiratory illness in a subject comprises providing PHPG at a final concentration of at least 0.05 ppm.

In a number of aspects, methods for treating a respiratory illness include exposing a subject to an environment having PHPG at a final concentration of at least 0.01 ppm. In an aspect, the concentration of PHPG may be at least 0.05 ppm. In an aspect, the concentration of PHPG may be at least 0.1 ppm. In another aspect, PHPG concentration may be 0.2 ppm. In yet another aspect, the PHPG concentration may be 0.25 ppm. In an aspect, the concentration of PHPG may be at least 0.4 ppm or 0.5 ppm. In an aspect, the concentration of PHPG may be at least 0.6 or 0.7 ppm. In another aspect, PHPG concentration may be up to 1.0 ppm. In yet another aspect, the PHPG concentration may be between 0.1 and 7.0 ppm.

In a number of aspects, a respiratory illness may be treated by exposing a subject, such as an animal or human, continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 0.5 ppm PHPG for at least 4 hours. In an aspect, the subject may be exposed to environment comprising at least 0.5 ppm PHPG 2, 3, 4, 5, 6, or more times in a 7 day period. In other aspects, exposing a subject to PHPG may be repeated regularly as a prophylactic measure.

In aspects according the present disclosure, improved lung function includes increasing static lung volume, increasing total lung capacity, increasing the partial pressure of oxygen in arterial blood gases, decreasing residual volume, or any combination thereof. Lung function may be measured using spirometry.

In a number of aspects, methods for improved lung function include exposing a subject to an environment having PHPG at a final concentration of at least 0.01 ppm. In an aspect, the concentration of PHPG may be at least 0.05 ppm. In an aspect, the concentration of PHPG may be at least 0.1 ppm. In another aspect, PHPG concentration may be 0.2 ppm. In yet another aspect, the PHPG concentration may be 0.25 ppm. In an aspect, the concentration of PHPG may be at least 0.4 ppm or 0.5 ppm. In an aspect, the concentration of PHPG may be at least 0.6 or 0.7 ppm. In another aspect, PHPG concentration may be up to 1.0 ppm. In yet another aspect, the PHPG concentration may be between 0.1 and 7.0 ppm.

In aspects according the present disclosure, a respiratory system is treated by exposing the subject to PHPG for at least 4 hours. In other aspects, exposure of a subject to PHPG is for at least 15, at least 30, at least 60, at least 90, at least 120, at least 180, at least 240, at least 300, at least 360, at least 420, or at least 480 consecutive minutes. In some aspects, treatment includes exposure to PHPG for at least 15, at least 30, at least 60, at least 90, or at least 120 minutes over a 24 hour, or 48 hour period. In other aspects, treatment includes exposure to PHPG for at least 8, at least 16 or at least 24 hours over a 7 day period. In some aspects, treatment includes exposure to PHPG for at least 1, 2, 3, 4, 5, 6, 7, 8, or more hours. In other aspects, treatment with PHPG is repeated 1, 2, 3, or more times daily, weekly, bi-weekly, or monthly.

In certain aspects, the amount of time of exposure may be decreased as the concentration of PHPG is increased. While non-toxic even at levels up to 7 ppm, it may be desirable to decrease the exposure level by decreasing the exposure time. As provided in further detail below, the methods of the present disclosure provide for exposing a subject to a "dose of PHPG." As used herein, a dose may be defined in "units" of PHPG equivalent to the concentration of PHPG in ppm multiplied by the number of hours a subject is exposed to the PHPG containing environment.

The present disclosure provides for, and includes, methods for treating a respiratory condition in a subject in need thereof comprising providing said subject in need with an environment comprising a purified hydrogen peroxide gas (PHPG) that is free of hydration and ozone at a final concentration of at least 0.01 parts per million (ppm). In another aspect, a method for treating a respiratory condition in a subject in need thereof may comprise providing PHPG at a final concentration of at least 0.05 ppm.

The present disclosure provides for, and includes, methods for reducing the severity of a respiratory infection in a subject comprising providing a purified hydrogen peroxide gas (PHPG) containing environment comprising PHPG that is free of hydration and ozone at a final concentration of at least 0.05 parts per million (ppm), and exposing the subject to said PHPG containing environment for a period of time, wherein the severity of the respiratory infection is reduced. In another aspect, the final concentration of PHPG may be 0.01 ppm.

In aspects according the present disclosure, the respiratory infection is selected from the group consisting of severe acute respiratory syndrome (SARS), Middle East Respiratory Syndrome (MERS), ebola, porcine reproductive and respiratory syndrome virus (PRRSV) infection, and respiratory syncytial virus (RSV).

In a number of aspects, methods for reducing the severity of a respiratory infection include exposing a subject to an environment having PHPG at a final concentration of at least 0.01 ppm. In an aspect, the concentration of PHPG may be at least 0.05 ppm. In an aspect, the concentration of PHPG may be at least 0.1 ppm. In another aspect, PHPG concentration may be 0.2 ppm. In yet another aspect, the PHPG concentration may be 0.25 ppm. In an aspect, the concentration of PHPG may be at least 0.4 ppm or 0.5 ppm. In an aspect, the concentration of PHPG may be at least 0.6 or 0.7 ppm. In another aspect, PHPG concentration may be up to 1.0 ppm. In yet another aspect, the PHPG concentration may be between 0.1 and 7.0 ppm.

In a number of aspects, methods for reducing the severity of a respiratory infection include exposing a subject, such as an animal or human, continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 0.5 ppm PHPG for at least 4 hours. In an aspect, the subject may be exposed to environment comprising at least 0.5 ppm PHPG 2, 3, 4, 5, 6, or more times in a 7 day period. In other aspects, exposing a subject to PHPG may be repeated regularly as a prophylactic measure.

The present disclosure provides for, and includes, methods for controlling a pathogen in the respiratory system of a subject comprising generating a purified hydrogen peroxide gas (PHPG) that is free of hydration and ozone to an environment, wherein the environment accumulates the PHPG at a final concentration of at least 0.05 parts per million, and exposing the subject to the PHPG containing environment for a period of time. In some aspects, the pathogen is selected from the group consisting of a virus, a bacterium, a fungus, and a parasite. In other aspects, the final concentration of PHPG is at least 0.01 ppm.

In aspects according to the present disclosure, the respiratory system includes one or more of the trachea, the bronchi, the conducting bronchioles, the respiratory bronchioles, the alveolar sac, the oral cavity, and the nasopharyngeal cavity.

In aspects according to the present disclosure, the fungus controlled, treated, or mitigated by the methods provided herein is from the genus *Aspergillus*. In other aspects, the fungus is selected from the group consisting of *Histoplasma capsulatum*, blastomyces, *Cryptococcus neoformans*, *Pneumocystis jiroveci*, *Coccidioides immitis*, *Blastomyces dermatitides*, *Pneumocystis provecii*, *Sporothrix schenckii*, *Cryptococcus neoformans*, *Aspergillus fumigatus*, and *Candida albicans*.

In aspects according to the present disclosure, the virus controlled, treated, or mitigated by the methods provided herein is a double stranded DNA virus, a single-stranded DNA virus, a double-stranded RNA virus, a positive sense single-stranded RNA virus, a negative sense single-stranded RNA virus, a single stranded RNA retrovirus, or a double-stranded DNA retrovirus.

In aspects according to the present disclosure, the bacterium controlled, treated, or mitigated by the methods provided herein is *Acinetobacter baumannii*, *Mycoplasma*, *Pneumococcus*, *Chlamydophila pneumoniae*, *Mycobacterium tuberculosis*, *Streptococcus pneumoniae*, *Haemophilus* species, or *Staphylococcus aureus*.

In aspects according to the present disclosure, the parasite controlled, treated, or mitigated by the methods provided herein is a protozoan, a nematode, or a trematode. In other aspects, the parasite is selected from the group consisting of *Toxoplasma gondii*, *Strongyloides stercoralis*, *Ascaris lumbricoides*, *Plasmodium malariae*, *Echinococcus granulosus*, *Dirofilaria immitis*, *Paragonimus westermani*, *Entamoeba histolytica*, *Ascaris lumbricoides*, *Ancylostoma duodenale*, *Necator americanus*, *Toxocara canis*, *Schistosoma mansoni*, *Schistosomahaematobiu*, *Schistosoma japonicum*, *Strongyloides stercoralis*, *Wuchereria bancrofti*, and *Brugia malayi*.

The present disclosure provides for, and includes, methods for preventing a respiratory infection comprising generating a hydrogen peroxide gas that is free of hydration and ozone; and providing the hydrogen peroxide gas to an environment wherein the environment accumulates the PHPG at a final concentration of at least 0.05 parts per million; and exposing a subject at risk for respiratory infection to the environment for at least four hours per day. In another aspect, a method for preventing a respiratory infection comprises generating a the hydrogen peroxide gas that is free of hydration and ozone; and providing the hydrogen peroxide gas to an environment wherein the environment accumulates the PHPG at a final concentration of at least 0.01 parts per million; and chronically exposing a subject at risk for respiratory infection to the environment for at least four hours per day. In other aspects, the subject at risk for respiratory infection may be continually exposed to PHPG at a concentration of 0.01 or 0.05 ppm.

The present disclosure provides for, and includes, methods for reducing the transmission of a respiratory infection from a first subject having the respiratory infection to a second subject not having the respiratory infection comprising: providing an environment comprising a purified hydrogen peroxide gas (PHPG) that is free of hydration and ozone at a final concentration of at least 0.05 parts per million; and exposing the first subject having the respiratory infection to the environment for one or more periods of time. In another aspect, the PHPG may be provided at a final concentration of at least 0.01 ppm to reduce transmission of a respiratory infection.

In a number of aspects, methods for reducing the transmission of a respiratory infection include exposing a subject to an environment having PHPG at a final concentration of at least 0.01 ppm. In an aspect, the concentration of PHPG may be at least 0.05 ppm. In an aspect, the concentration of PHPG may be at least 0.1 ppm. In another aspect, PHPG concentration may be 0.2 ppm. In yet another aspect, the PHPG concentration may be 0.25 ppm. In an aspect, the concentration of PHPG may be at least 0.4 ppm or 0.5 ppm. In an aspect, the concentration of PHPG may be at least 0.6 or 0.7 ppm. In another aspect, PHPG concentration may be up to 1.0 ppm. In yet another aspect, the PHPG concentration may be between 0.1 and 7.0 ppm.

In a number of aspects, methods for reducing the transmission of a respiratory infection include exposing a subject, such as an animal or human, continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 0.5 ppm PHPG for at least 4 hours. In an aspect, the subject may be exposed to environment comprising at least 0.5 ppm PHPG 2, 3, 4, 5, 6, or more times in a 7 day period. In other aspects, exposing a subject to PHPG may be repeated regularly.

The present disclosure provides for, and includes, methods for supplementing endogenous $H_2O_2$ in the lung of a subject comprising exposing said subject to an environment comprising a purified hydrogen peroxide gas (PHPG) that is free of hydration and ozone, wherein the environment accumulates said PHPG at a final concentration of at least 0.05 parts per million. In another aspect, the endogenous $H_2O_2$ in the lung may be supplemented by exposing a subject to a PHPG concentration of 0.01 ppm.

The present disclosure provides for, and includes, methods for stimulating the host defenses to a respiratory infection of a subject comprising providing an environment comprising a purified hydrogen peroxide gas (PHPG) that is free of hydration and ozone at a final concentration of at least 0.01 parts per million; and exposing the subject to said environment for one or more periods of time, thereby increasing the level of hypothiocyanate ion in the lungs of said subject. In another aspect, a method for stimulation the host defenses to a respiratory infection of a subject comprises providing purified hydrogen peroxide gas (PHPG) at a final concentration of at least 0.01 ppm.

The present disclosure provides for, and includes, methods for managing a condition affecting the lungs of a subject comprising generating a purified hydrogen peroxide gas (PHPG) that is free of hydration and ozone to an environment wherein the environment accumulates the PHPG at a final concentration of at least 0.05 parts per million, and exposing said subject to the PHPG containing environment for a period of time. In other aspects, the PHPG concentration may be at least 0.01 ppm. In aspects according to the present disclosure, the condition is selected from the group consisting of chronic obstructive pulmonary disease (COPD), pneumonia, an allergy, asthma, prematurity, and cystic fibrosis.

In one aspect of the present disclosure, exposing to PHPG is in combination with a respiratory therapy selected from the group consisting of deep breathing exercises, postural drainage, incentive spirometry, and chest physiotherapy.

The present disclosure provides for, and includes, methods for decreasing the severity of a respiratory infection in a subject comprising providing an environment comprising a purified hydrogen peroxide gas (PHPG) that is free of hydration and ozone at a final concentration of at least 0.05 parts per million; and exposing the subject to the environment for one or more periods of time, wherein the severity of the respiratory infection is decreased. In other aspects, the severity of a respiratory infection may be reduced by providing PHPG at a concentration of 0.01 ppm.

The present disclosure provides for, and includes, methods for increasing the rate of hypothiocyanate ion production catalyzed by lactoperoxidase (LPO) in the lungs of a subject comprising providing an environment comprising a purified hydrogen peroxide gas (PHPG) that is free of hydration and ozone at a final concentration of at least 0.05 parts per million; and exposing the subject to the environment for one or more periods of time. In another aspect, the PHPG may be provided at 0.01 ppm to increase the rate of hypothiocyanate ion production catalyzed by lactoperoxidase (LPO) in the lungs of a subject.

The present disclosure provides for, and includes, methods for improving the lung function of a subject comprising: providing an environment comprising a purified hydrogen peroxide gas (PHPG) that is free of hydration and ozone at a final concentration of at least 0.05 parts per million; and exposing the subject to the environment for one or more periods of time. In another aspect, the final concentration of PHPG for improving lung function may be at least 0.01 ppm.

The present disclosure provides for, and includes, the use of a purified hydrogen peroxide gas (PHPG) for the preparation of an environment suitable for preventing, treating, or controlling a respiratory illness in a subject comprising: generating a hydrogen peroxide gas that is free of hydration and ozone; and providing the hydrogen peroxide gas to an environment wherein the environment accumulates the PHPG at a final concentration of at least 0.05 parts per million. In an aspect, an environments suitable for preventing, treating, or controlling a respiratory illness in a subject includes an environment having 0.01 ppm PHPG.

In a number of aspects, the use of a Purified Hydrogen Peroxide Gas (PHPG) for the preparation of an environment suitable for preventing, treating, or controlling a respiratory illness includes introducing PHPG into an enclosed space and maintaining a concentration of PHPG ranging between 0.01 and 7.0 ppm. In certain aspects, the PHPG may be maintained at a concentration above 0.2 ppm. In yet another aspect, the PHPG may be maintained at a concentration above 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

The present disclosure provides for, and includes, methods for reducing mortality due to respiratory illness in a subject comprising providing an environment comprising a PHPG that is free of hydration and ozone at a final concentration of at least 0.01 parts per million (ppm); and exposing the subject to the environment for at least one period of time. In a number of aspects, methods for reducing mortality include exposing a subject to an environment having PHPG at a final concentration of at least 0.01 ppm. In an aspect, the concentration of PHPG may be at least 0.05 ppm. In an aspect, the concentration of PHPG may be at least 0.1 ppm. In another aspect, PHPG concentration may be at least 0.2 ppm. In yet another aspect, the PHPG concentration may be at least 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

In a number of aspects, methods for reducing mortality include exposing a subject continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 0.5 ppm PHPG for at least 4 hours. In an aspect, the subject may be exposed to environment comprising at least 0.5 ppm PHPG 2, 3, 4, 5, 6, or more times in a 7 day period. In other aspects, exposing a subject to PHPG may be repeated regularly.

The present disclosure provides for, and includes, methods for preparing an environment suitable for occupancy of a subject comprising: providing a device for producing purified hydrogen peroxide gas (PHPG), wherein said PHPG is free of hydration and ozone, and wherein the environment has a reduced level of infectious agents, allergens, or a combination thereof.

In aspects according to the present disclosure, the exposure of a subject to a PHPG containing environment may be described as a "dose of PHPG". As used herein, a dose may be defined in "units" of PHPG equivalent to the concentration of PHPG in ppm multiplied by the number of hours a subject is exposed to the PHPG containing environment. For example, the dose of PHPG to a subject exposed to an environment having 0.01 ppm PHPG for 1 hour is 0.01 units of PHPG. A subject exposed to an environment comprising 0.5 ppm PHPG for 5 hours receives an effective dose of 2.5 units of PHPG.

In an aspect according to the present disclosure, a subject is exposed to an environment having a PHPG concentration of at least 0.01 ppm for at least 0.5 hours (minimum dose of 0.05 units of PHPG). In a other aspect, the subject is exposed to PHPG at a dose of at least 0.1, 0.2, 0.3, 0.4, 0.5, 1.0, 1.5, 2.0, 5.0, or at least 10.0 per day. In some aspects, the subject is exposed up to a maximum dose of 24 units of PHPG per day. In one aspect, the methods for improving the health of a subject including prophylaxis, mitigation, or treatment of a medical condition include exposing the subject to a dose of PHPG between about 0.02 and about 0.06 units of PHPG per day.

In an aspect according the present disclosure, the subject is exposed to the minimum dose of PHPG on a daily basis. In other aspects the subject is exposed to the minimum dose of PHPG at least twice per week. In another aspect, the subject is exposed to PHPG at least 3, 4, 5, 6, or 7 times per week. In some aspects, the subject is exposed to PHPG more than once per day.

In an aspect according to the present disclosure, the subject is exposed to the minimum dose of PHPG at least 5 times per month. In another aspect, the subject is exposed to PHPG at least 10, 15, 20, or 25 times per month. In one aspect, the subject is exposed to the minimum dose of PHPG Monday through Friday at least once, twice, or 3 times per month.

In an aspect according to the present disclosure, the subject is exposed to an environment having a PHPG concentration of at least 0.02 ppm, at least 0.05 ppm, at least 0.1, at least 0.2, or at least 0.5 ppm for at least 0.5 hours. In other aspects, the subject is exposed to these PHPG concentrations for at least 1, 2, 3, 4, 5, 6, 7, or at least 8 hours per day.

In certain aspects, the amount of PHPG may vary from about 0.005 ppm to about 0.10 ppm, more particularly from about 0.02 ppm to about 0.05 ppm, in the environment. In certain aspects, the amount of PHPG may vary from about 0.005 ppm to about 0.40 ppm. PHPG levels of 0.2 ppm using a feed of untreated air containing absolute humidity as low as 3.5 mg/L can consistently be achieved. More particularly, PHPG levels from about 0.09 ppm to about 0.13 ppm using humid re-circulated air can be produced in the environment to be treated.

In certain aspects of the present disclosure, the humidity of the ambient air is preferably above about 1% relative humidity (RH), above about 5% RH, above about 10% RH, etc. In certain aspects, the humidity of the ambient air may be between about 10% and about 99% RH. In one aspect, the method of the present disclosure includes regulating the humidity of the ambient air within the range of about 5% to about 99% RH, or about 10% to about 99% RH.

Poor indoor air quality is one of the major factors that induce allergies and produce respiratory infections in humans. Confined spaces also lead to other infections in subjects, such as humans or animals. The presence of microorganisms, toxins, and allergens is mainly due to poor ventilation, excess moisture, and improper cleaning and disinfection. Fungi, bacteria, and parasites (e.g., mites, lice) produce these allergens. There are several known procedures that can reduce the concentration of these allergens by reduction or elimination of their sources in the closed environment, but they are generally based on chemicals that are harmful to humans and animals.

The present disclosure provides for and includes method of treating sinusitis. One of the respiratory problems due to poor indoor air quality is sinusitis. Sinusitis may be caused by bacteria (e.g., *streptococci, staphylococci, pneumococci, Haemophilus influenza*), viruses (e.g., rhinovirus, influenza virus, parainfluenza virus), or fungi (e.g., *Aspergillus, Dematiaceae, Mucoraceae, Penicillium* sp.). The incidence of sinusitis (or inflammation of the sinuses) appears to be increasing. Health care experts estimate that 37 million Americans are affected by sinusitis every year. Americans spend millions of dollars each year for medications for their sinus symptoms.

In an aspect of the present disclosure, a method for treating sinusitus is provided comprising exposing a subject to a PHPG environment for a period of time. In an aspect, a subject having sinusitis inhabits a PHPG environment having at least 0.01 ppm PHPG for at least an average of four hours per day. In other aspects, PHPG is provided at a concentration of at least 0.05 ppm. In aspects according to the present disclosure, a subject may have acute sinusitis, subacute sinusitis, chronic sinusitis or recurrent sinusitis. Importantly, the underlying cause of the sinusitis in the subject need not be known to benefit from treatment with PHPG. In an aspect, the sinusitis may be caused by a fungus, a bacteria, a virus or an allergen.

Bacteria are the most common infectious agents in sinusitis and bacterial sinusitis is treatable using the methods of the present disclosure. The bacteria most commonly implicated in sinusitis are *Streptococcus pneumoniae* (also called pneumococcal pneumonia or pneumococci), *Haemophilus influenzae*, and *Moraxella catarrhalis*. Each are treatable according to the methods of the present disclosure. Less common bacterial culprits include other streptococcal strains (including Group A *Streptococcus*) and *Staphylococcus aureus*. Additionally, coagulase-negative *staphylococci*, alpha-hemolytic streptococci, and enteric bacilli can be found in chronic sinusitis and are treatable by exposure of a subject to a PHPG containing environment.

Also a provided herein, sinusitis treatable by the present methods may be caused by fungus. In certain aspects, a subject in need of treatment for sinusitis caused by a fungus may have additional underlying conditions including subjects with diabetes, leukemia, AIDS, or other conditions that impair the immune system. Less commonly, fungal infections can also occur in patients with healthy immune systems. Subjects having fungal sinusitis due to allergic-type reactions are also treatable using the methods of the present disclosure.

In an aspect, a fungal sinusitis treatable by the present methods may originate from the classes Zygomycetes (*Mucor* spp.) and Ascomycetes (*Aspergillus* spp.). In another aspect, fungal sinusitis treatable by exposure to a PHPG containing environment may be *Aspergillis*, the most common cause of fungal sinusitis. In other aspects, the fungal sinusitis may be caused by *Curvularia, Bipolaris, Exserohilum*, or *Mucormycosis*. In further aspects, the present methods provide for the treatment of three major types of fungus—*Penicillum, Stachybotrys*, and *Aspergillus*—that pose particular threats to human health and are the most predominant fungi found in air sampling. Importantly, providing a PHPG containing environment also reduces, mitigates or eliminates the fungal spores and hyphae. However, in certain aspects, a subject exposed to a fungus benefits from PHPG even where the exposure occurs in an untreated environment.

The present disclosure provides for, and includes methods of treating laboratory animals by exposing the laboratory animals to a PHPG containing environment. There are presently at least 1300 research facilities and 223 federal agencies registered with the U.S. Department of Agriculture (USDA) that use registered laboratory animals. (Crawford, "A review of the animal welfare enforcement report data, 1973-1995," AWIC Newsletter, Summer 1996). In addition to mortality and clinical disease, it is known that many laboratory animals suffer from subclinical infections, in which overt signs of disease are not observed. Laboratory animals are particularly sensitive to the air quality of enclosed spaces because of their number, diversity and proximity and that they exist in enclosed facilities. Thus, once a respiratory pathogen enters a facility, it becomes difficult to remove and prevent transmission. Moreover, sacrifice of animals may not be feasible when the animals are part of ongoing studies.

The present disclosure provides for, and includes, methods for treating laboratory animals comprising providing purified hydrogen peroxide gas (PHPG) that is free of hydration and ozone at a final concentration of at least 0.01 parts per million (ppm), and exposing the laboratory animals to the environment for one or more periods of time. In an aspect, the concentration of PHPG may be at least 0.05 ppm. In an aspect, the concentration of PHPG may be at least 0.1 ppm. In another aspect, PHPG concentration may be at least 0.2 ppm. In yet another aspect, the PHPG concentration may be at least 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

In a number of aspects, laboratory animals may be treated continuously in a facility with levels of PHPG ranging between 0.01 and 7.0 ppm. In certain aspects, laboratory animals may be treated with PHPG ranging from 0.01 to 5.0 ppm for less than a full day. In an aspect, a laboratory animal may be exposed to these PHPG concentrations for at least 1, 2, 3, 4, 5, 6, 7, or at least 8 hours per day. In another aspect, a laboratory animal may be exposed to an environment comprising at least 1.0, 2.0, 3.0, 4.0, 5.0, 6.0, or at least 7.0 ppm PHPG for at least 8 hours. In yet other aspects, a laboratory animal may be continuously treated at low levels of PHPG and provided high levels of PHPG when infection is identified or when an infection has been introduced into a facility.

The present disclosure provides for, and includes, methods for managing a condition affecting the lungs of a subject comprising generating a purified hydrogen peroxide gas (PHPG) that is free of hydration and ozone to an environment wherein the environment accumulates the PHPG at a final concentration of at least 0.01 parts per million, and exposing the subject to the PHPG containing environment for a period of time. In aspects according the present disclosure, the condition is selected from the group consisting of chronic obstructive pulmonary disease (COPD), pneumonia, an allergy, asthma, prematurity, and cystic fibrosis.

The present disclosure provides for, and includes, methods for managing COPD comprising exposing a subject to an environment having a PHPG concentration of at least 0.01 ppm. In an aspect, the concentration of PHPG may be at least 0.05 ppm. In an aspect, the concentration of PHPG may be at least 0.1 ppm. In another aspect, PHPG concentration may be at least 0.2 ppm. In yet another aspect, the PHPG concentration may be at least 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

In a number of aspects, COPD may be managed by exposing a subject continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 1.0, 2.0, 3.0, 4.0, 5.0, 6.0, or at least 7.0 ppm PHPG for at least 8 hours.

The present disclosure provides for, and includes, methods for managing pneumonia comprising exposing a subject to an environment having a PHPG concentration of at least 0.02 ppm. In an aspect, the concentration of PHPG may be at least 0.05 ppm. In an aspect, the concentration of PHPG may be at least 0.1 ppm. In another aspect, PHPG concentration may be at least 0.2 ppm. In yet another aspect, the PHPG concentration may be at least 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

In a number of aspects, pneumonia may be managed by exposing a subject continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 1.0, 2.0, 3.0, 4.0, 5.0, 6.0, or at least 7.0 ppm PHPG for at least 8 hours.

The present disclosure provides for, and includes, methods for managing an allergy comprising exposing a subject to an environment having a PHPG concentration of at least 0.02 ppm. In an aspect, the concentration of PHPG may be at least 0.05 ppm. In an aspect, the concentration of PHPG may be at least 0.1 ppm. In another aspect, PHPG concentration may be at least 0.2 ppm. In yet another aspect, the PHPG concentration may be at least 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

In a number of aspects, an allergy may be managed by exposing a subject continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 1.0, 2.0, 3.0, 4.0, 5.0, 6.0, or at least 7.0 ppm PHPG for at least 8 hours.

The present disclosure provides for, and includes, methods for managing asthma comprising exposing a subject to an environment having a PHPG concentration of at least 0.02 ppm. In an aspect, the concentration of PHPG may be at least 0.05 ppm. In an aspect, the concentration of PHPG may be at least 0.1 ppm. In another aspect, PHPG concentration may be at least 0.2 ppm. In yet another aspect, the PHPG concentration may be at least 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

In a number of aspects, asthma may be managed by exposing a subject continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 1.0, 2.0, 3.0, 4.0, 5.0, 6.0, or at least 7.0 ppm PHPG for at least 8 hours.

The present disclosure provides for, and includes, methods for managing a pulmonary condition associated with prematurity comprising exposing a subject to an environment having a PHPG concentration of at least 0.02 ppm. In an aspect, the concentration of PHPG may be at least 0.05 ppm. In an aspect, the concentration of PHPG may be at least 0.1 ppm. In another aspect, PHPG concentration may be at least 0.2 ppm. In yet another aspect, the PHPG concentration may be at least 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

In a number of aspects, a pulmonary condition associated with prematurity may be managed by exposing a subject continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 1.0, 2.0, 3.0, 4.0, 5.0, 6.0, or at least 7.0 ppm PHPG for at least 8 hours.

The present disclosure provides for, and includes, methods for managing cystic fibrosis comprising exposing a subject to an environment having a PHPG concentration of at least 0.02 ppm. In an aspect, the concentration of PHPG may be at least 0.05 ppm. In an aspect, the concentration of PHPG may be at least 0.1 ppm. In another aspect, PHPG concentration may be at least 0.2 ppm. In yet another aspect, the PHPG concentration may be at least 0.25 ppm. In an aspect, the concentration of PHPG may be at least 0.4 ppm or at least 0.5 ppm. In an aspect, the concentration of PHPG may be at least 0.6 or at least 0.7 ppm. In another aspect, PHPG concentration may be up to 1.0 ppm. In yet another aspect, the PHPG concentration may be between 0.1 and 7.0 ppm.

In a number of aspects, cystic fibrosis may be managed by exposing a subject continuously in a facility with levels of PHPG ranging between 0.01 and 7.0 ppm. In certain aspects, the subject may be exposed to PHPG ranging from 0.01 to 5.0 ppm for less than a full day. In an aspect, a subject may be exposed to these PHPG concentrations for at least 1, 2, 3, 4, 5, 6, 7, or at least 8 hours per day. In another aspect, the subject may be exposed to an environment comprising at least 1.0, 2.0, 3.0, 4.0, 5.0, 6.0, or at least 7.0 ppm PHPG for at least 8 hours.

One of ordinary skill in the art would understand that the length of exposure to PHPG and the total number of exposures to PHPG in the methods described above may be varied to achieve the same or improved effect. A skilled artisan can determine without undue experimentation whether higher concentrations of PHPG or longer exposure periods to PHPG result in further improvement. For each concentration of PHPG recited above, the length of exposure may be greater than 0.5 hours or less than 24 hours per day. The length of exposure may be at least 4 hours or at least 8 hours in a day. These exposures to PHPG may be repeated as many times as necessary to achieve improved benefit.

While the disclosure has been described with reference to preferred aspects, it will be understood by those skilled in the art that various changes may be made and equivalents may be substituted for elements thereof to adapt to particular situations without departing from the scope of the disclosure. Therefore, it is intended that the disclosure not be limited to the particular aspects disclosed as the best mode contemplated for carrying out this disclosure, but that the disclosure will include all aspects falling within the scope and spirit of the appended claims.

EXAMPLES

Example 1: Four Families Using PHPG Technology in Their Homes

PHPG technology was deployed in the homes of four subject families having a total of 13 members including four children between the ages of birth and six. Over a period of three years, none of the subjects contracted cold, flu, or other respiratory illness while using PHPG technology, despite extensive and regular exposures at work, in public venues, and in day care and school environments. It is estimated that the period of exposure ranged from about 8 hours daily to about 24 hours at a PHPG level of at least about 0.2 ppm. Discontinuous exposure to the PHPG containing environment did not have an adverse effect on the resistance to respiratory infection. Resistance to respiratory infection appeared to extend beyond the protected environment demonstrating the persistent effects of habitation in the presence of PHPG on the innate defense mechanisms of the respiratory system.

Example 2: Major League Baseball Team Spring Training

PHPG technology was installed in the Florida facilities of a major league baseball team in January, 2014. Each year for spring training and tryouts over 300 veteran and prospective players are brought to Florida for training beginning in January. Players converge from all corners of the US, and from other countries including those with limited modern healthcare and sanitation. Accordingly, these diverse players bring various illnesses from their points of origin, which in previous years spread through the player population. Historically, two to five players miss three to four days of training per week over a ten week period. During the 2014 training and tryout period, with exposure to the PHPG containing environment, only one player missed one training day due to illness during spring training. It is estimated that the players were exposed to the PHPG environment for about 4 hours per day on average at a PHPG level of about 0.3 ppm, while using facilities such as the weight room, locker room, cafeteria, and medical facilities. The significant and notable improvement in overall team health was unexpected given the limited amounts of time that an average player was exposed to the PHPG containing environment. Given the limited exposure, resistance to infection appears to carry beyond the environment and demonstrates the persistent effects of exposure to PHPG on the innate defense mechanisms of the respiratory system. Players exhibited reduced infection rates despite contact with the general population outside of the environment.

Example 3: Individual with History of Mustard Agent Exposure

In 2007, a prototype PHPG generative device was installed for testing purposes in the dwelling of an individual who had been previously exposed to chloromethyl-methyl-sulfide in 1992. Exposure to chloromethyl-methyl-sulfide resulted in the temporary loss of more than 50% lung function temporarily, followed by a recovery of a portion thereof. Subject individual worked in Manhattan and regularly used public transportation between 2004 and 2006 and suffered from chronic bronchitis over the winter months, as well as regular colds and flu. Following installation of the prototype PHPG generating device, the subject spent an average of eight hours per day in his apartment having an estimated PHPG level of about 0.05 ppm. Normal day to day routine was maintained including office work in Manhattan and daily commutes on public transportation.. During the period between the fall of 2007 and the spring of 2008 the subject did not suffer bronchitis, colds, or flu after obtaining the prototype despite regular daily exposures while outside the protected environment of his apartment. Given the limited exposure, resistance to infection appears to carry beyond the environment and demonstrates the persistent effects of exposure to PHPG on subjects exposed daily to a PHPG containing environment.

What is claimed:

1. A method for treating a respiratory illness in a subject in need thereof comprising:
providing an enclosed space for treatment comprising a purified hydrogen peroxide gas (PHPG) that is substantially free of hydration and ozone at a final concentration of at least 0.01 parts per million (ppm); and
treating said subject in need by exposing said subject to said environment for at least one period of time to provide a therapeutic amount of PHPG, wherein said treating reduces the severity of a respiratory infection or reduces the duration of a respiratory infection wherein said subject in need thereof is a human and is infected by an influenza virus, a severe acute respiratory syndrome (SARS) virus, a Middle East Respiratory Syndrome (MERS) virus, or a respiratory syncytial virus (RSV), wherein said subject in need has a respiratory infection.

2. The method of claim 1, wherein said reduction of the severity of respiratory infections is a reduction in one or more of nasal congestion, runny nose (rhinorrhea), nasal discharge, nasal breathing, sneezing, sore or scratchy throat, painful swallowing (odynophagia), cough, malaise, or fever.

3. The method of claim 1, wherein said treating comprises reducing the duration of said respiratory infection.

4. The method of claim 1, wherein said period time is at least 8 hours over a 7 day period.

5. The method of claim 1, wherein the total time of exposure is at least 1 hours.

6. The method of claim 1, wherein said exposing is repeated 1 or more times daily, weekly, bi-weekly, or monthly.

7. The method of claim 1, wherein said environment comprises PHPG at a final concentration of at least 0.1 ppm.

8. The method of claim 1, wherein said therapeutic amount is at least 0.1 units of PHPG.

9. The method of claim 1, wherein said therapeutic amount is at least 0.5 units of PHPG.

10. The method of claim 1, wherein said therapeutic amount is provided at least once per day.

* * * * *